United States Patent [19]

Wacks

[11] Patent Number: 5,360,410
[45] Date of Patent: Nov. 1, 1994

[54] SAFETY SYRINGE FOR MIXING TWO-COMPONENT MEDICAMENTS

[75] Inventor: Jonathan L. Wacks, Forest Hills, N.Y.

[73] Assignee: Senetek PLC, St. Louis, Mo.

[21] Appl. No.: 740,843

[22] Filed: Aug. 6, 1991

Related U.S. Application Data

[63] Continuation-in-part of Ser. No. 641,752, Jan. 16, 1991.

[51] Int. Cl.⁵ .......................... A61M 5/00; A61M 5/24
[52] U.S. Cl. ..................................... 604/232; 604/87; 604/88; 604/110; 604/191; 604/205; 604/206; 604/416; 604/415
[58] Field of Search ................ 604/82, 87–91, 604/187, 110, 191, 195, 196, 198, 200, 201, 205, 206, 218, 232, 234, 236, 237, 403, 411–416; 222/386, 390, 391

[56] References Cited

U.S. PATENT DOCUMENTS

| | | |
|---|---|---|
| 2,345,301 | 3/1944 | Smith . |
| 2,701,566 | 2/1955 | Krug . |
| 2,832,339 | 4/1958 | Sarnoff et al. . |
| 2,876,770 | 3/1959 | White . |
| 3,395,704 | 8/1968 | Frey et al. . |
| 4,055,177 | 10/1977 | Cohen . |
| 4,108,177 | 8/1978 | Pistor . |
| 4,178,928 | 12/1979 | Tischlinger .................. 604/202 |
| 4,316,463 | 2/1982 | Schmitz et al. ............... 604/194 |
| 4,328,802 | 5/1982 | Curley et al. . |
| 4,499,148 | 2/1985 | Goodale et al. . |
| 4,553,962 | 11/1985 | Brunet ......................... 604/232 |
| 4,617,016 | 10/1986 | Blomberg . |
| 4,664,653 | 5/1987 | Sagstetter et al. ............. 604/194 |
| 4,689,042 | 8/1987 | Sarnoff et al. ................ 604/191 |
| 4,693,706 | 9/1987 | Ennis, III ...................... 604/87 |
| 4,719,825 | 1/1988 | LaHaye et al. . |
| 4,755,169 | 7/1988 | Sarnoff et al. ................ 604/89 |
| 4,767,413 | 8/1988 | Haber et al. .................. 604/232 |
| 4,781,700 | 11/1988 | Vicario ......................... 604/234 |
| 4,808,184 | 2/1989 | Topic ........................... 604/56 |
| 4,834,717 | 5/1989 | Haber et al. .................. 604/232 |
| 4,931,040 | 6/1990 | Haber et al. . |
| 4,936,833 | 6/1990 | Sams ........................... 604/232 |
| 4,950,246 | 8/1990 | Muller . |
| 4,955,869 | 9/1990 | Bin . |
| 4,968,229 | 11/1990 | Ahlstrand et al. ............. 604/232 |
| 4,968,299 | 11/1990 | Ahlstrand et al. ............. 604/90 |
| 4,968,302 | 11/1990 | Schluter et al. .............. 604/135 |
| 4,983,164 | 1/1991 | Hook et al. . |
| 5,092,842 | 3/1992 | Bechtold et al. .............. 604/232 |
| 5,094,148 | 3/1992 | Haber et al. .................. 604/218 |
| 5,098,382 | 3/1992 | Haber et al. .................. 604/232 |
| 5,112,317 | 5/1992 | Michel ......................... 604/232 |
| 5,114,406 | 5/1992 | Gabriel et al. ................ 604/232 |

OTHER PUBLICATIONS

Variject–2–Kammerspritze, Variject Two-Compartment Syringe.

*Primary Examiner*—C. Fred Rosenbaum
*Assistant Examiner*—Ronald Stright, Jr.
*Attorney, Agent, or Firm*—Fitch, Even, Tabin & Flannery

[57] ABSTRACT

A disposable two-component safety syringe with retractable injection needle adapted for the separate storage of medicament and medicament solvent and the pre-injection mixing thereof. The cartridge-type syringe is adapted to be used manually or in conjunction with an automatic injection/aspiration device for breaching a temporary seal between chambers for the medicament and medicament solvent immediately prior to injection are also provided. Pre-measured medicament is provided in a form which requires no pre-injection agitation. The cartridge is also provided with an injection needle disposed completely within the cartridge housing for safely and sanitarily withdrawing the injection needle to reside completely within the disposable cartridge after use. In one embodiment of the invention, a pushrod for automatically agitating the mixing components is provided.

13 Claims, 14 Drawing Sheets

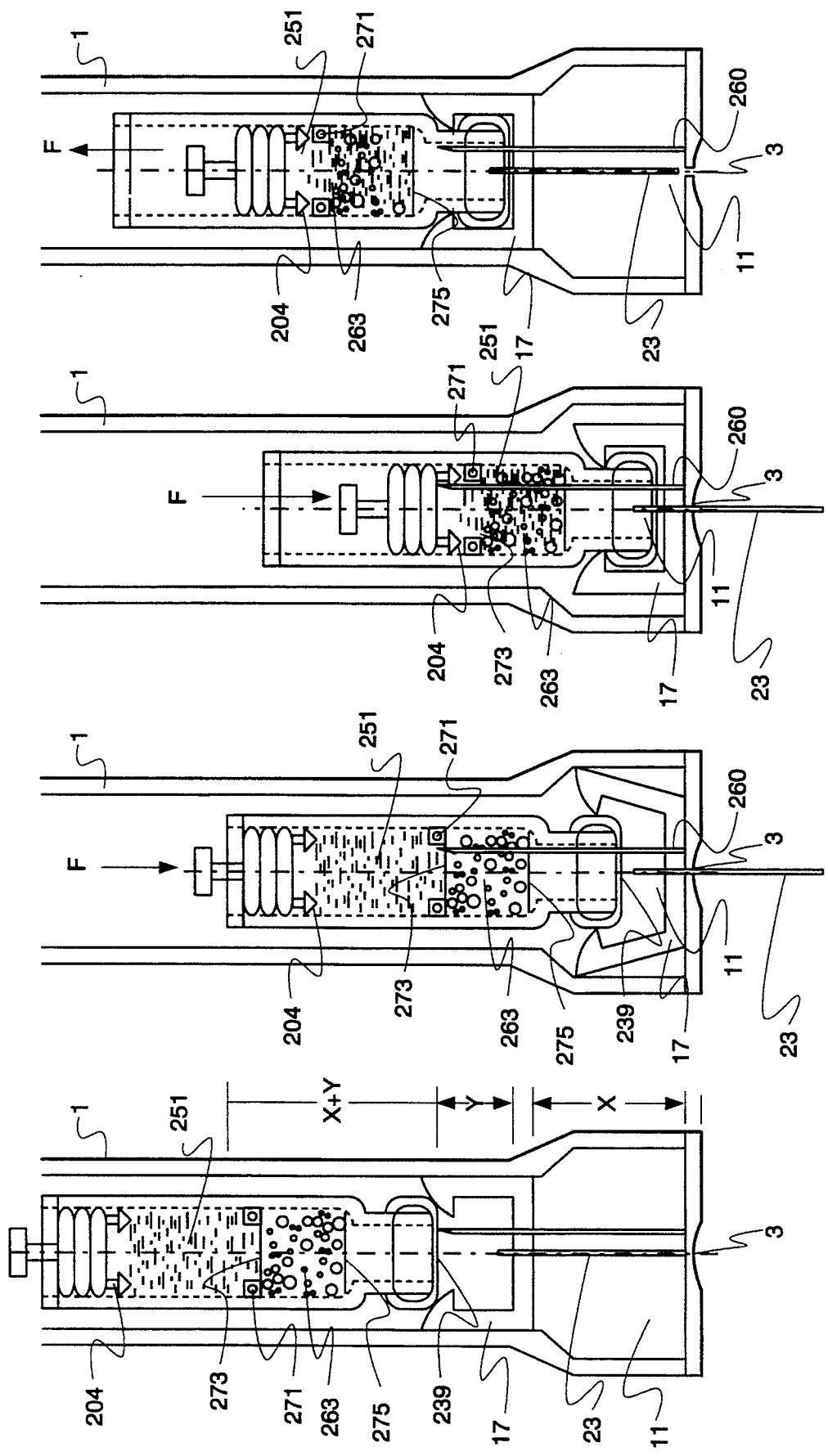

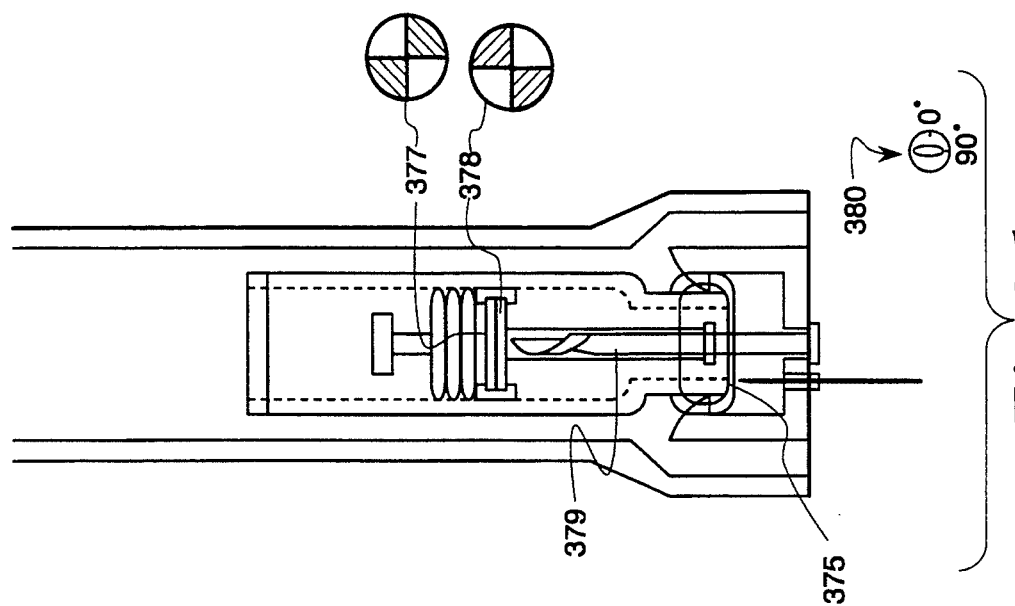
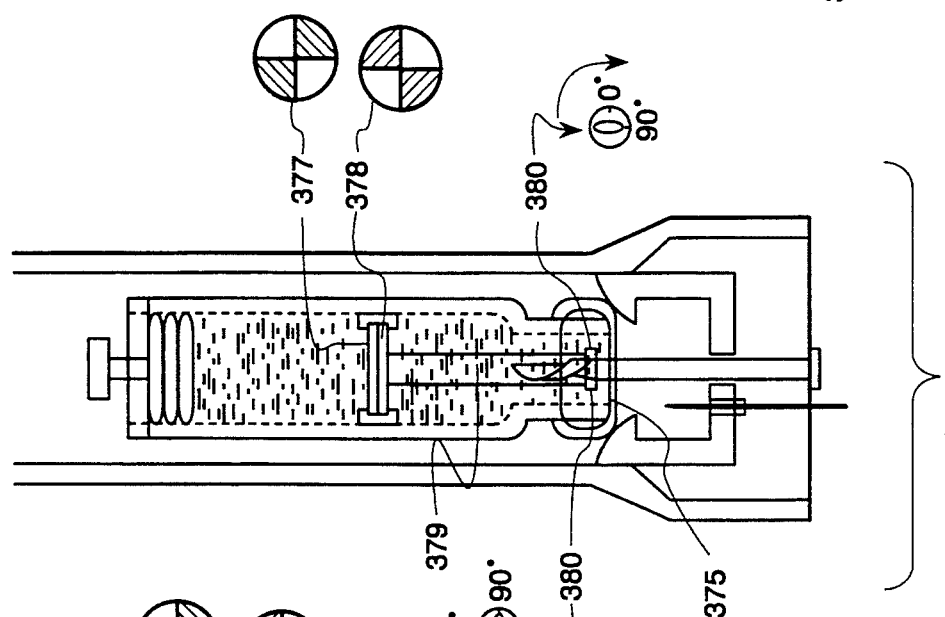
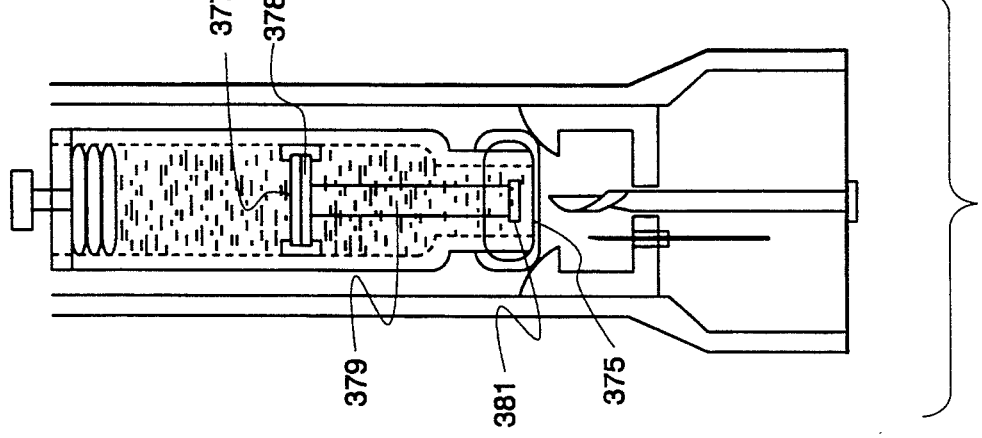

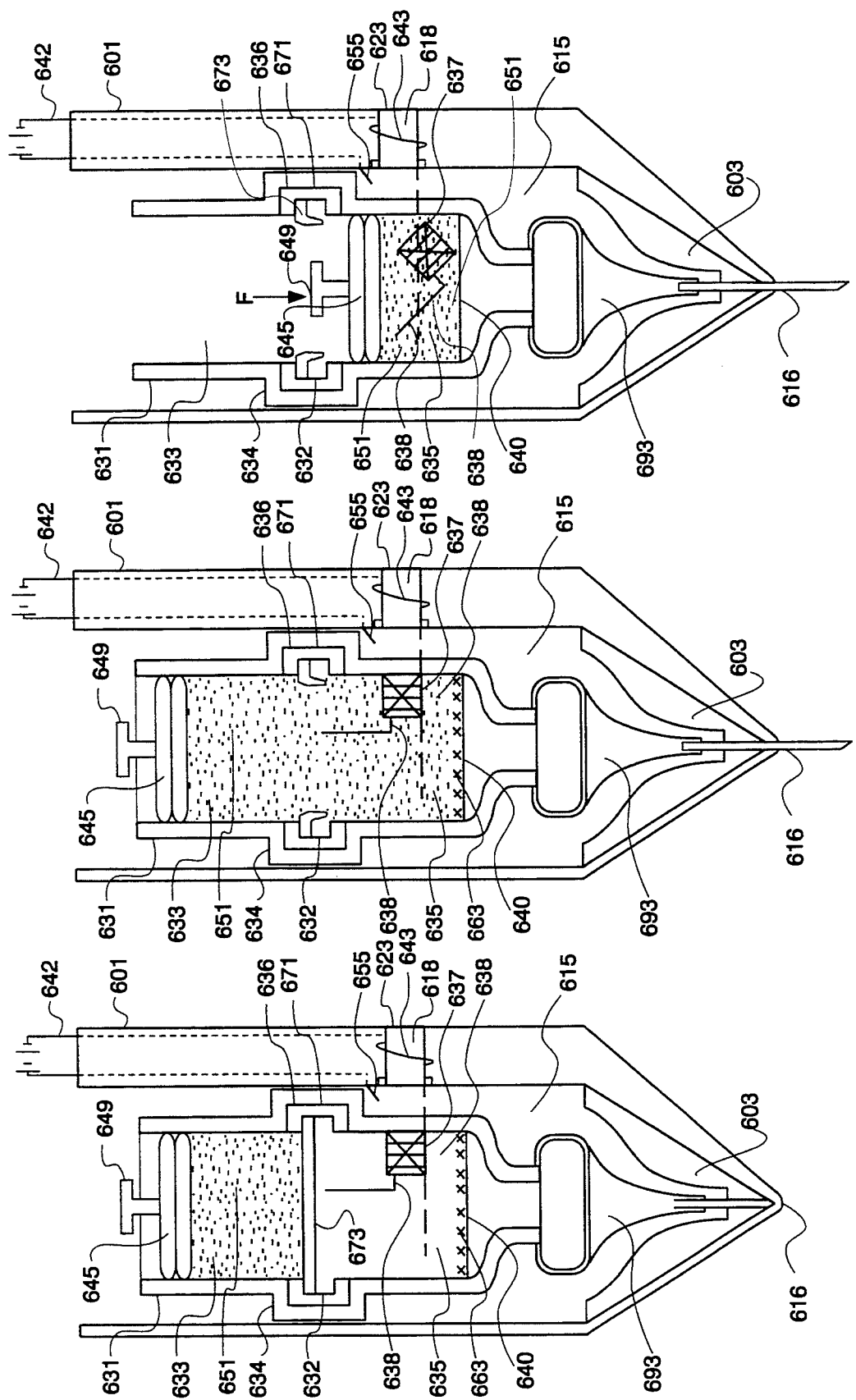

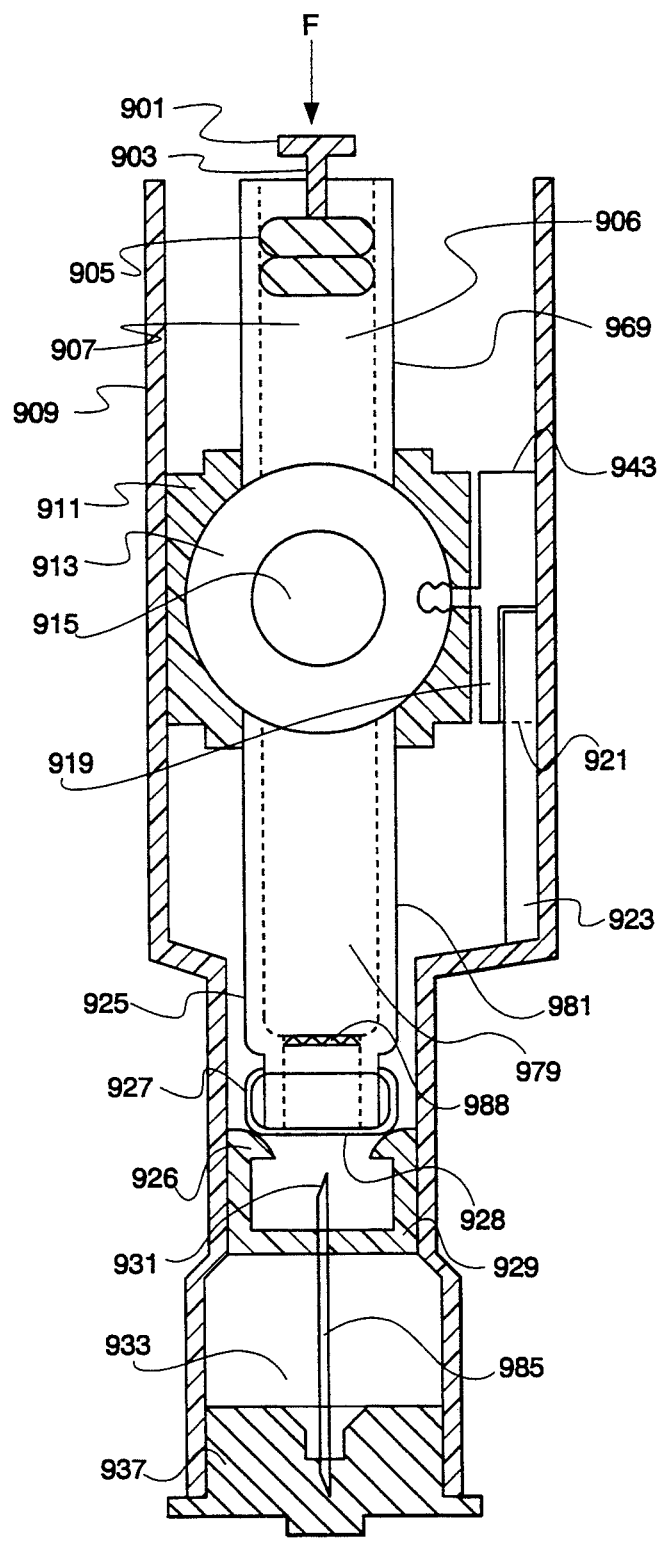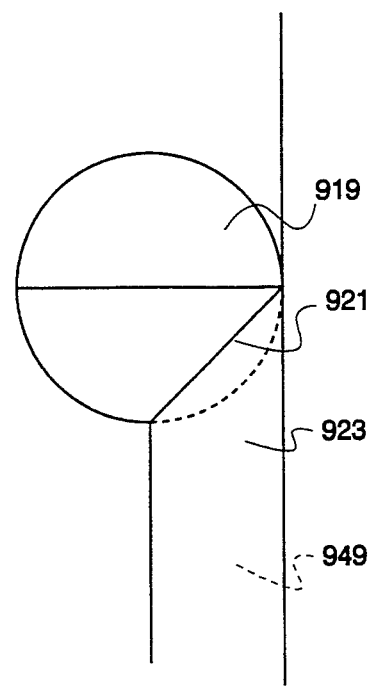
Fig. 9a
Fig. 9b

SAFETY SYRINGE FOR MIXING TWO-COMPONENT MEDICAMENTS

This application is a continuation-in-part of application Ser. No. 641,752, filed Jan. 16, 1991 for a Programmable Automatic Injector and Vial with Retracting Needle, inventor, Jonathan Wacks. Application Ser. No. 641,752, pending, is hereby incorporated by reference.

BACKGROUND OF THE INVENTION

The present invention relates to a two-component safety injection syringe for medical and research purposes and more particularly to a device designed to separately store a medicament and a solvent therefor until a time just prior to injection when the two substances are mixed and then injected.

It is well known in the medical field that the shelf life of particular pharmaceutically or medically active substances is increased when the active substance is stored in a dry form or in stable but non-injectable solution form prior to injection. Many drugs now being marketed or being developed for marketing are not stable in their deliverable solutions for a sufficient period of time to allow for commercial distribution or have shelf lives which are unacceptably short. Among these pharmaceuticals are epinephrine, which is used to treat severe allergic and anaphylactic reactions, and cyclophosphamide, an anti-cancer substance. Other pharmaceutically active substances such as urokinase, which is used for dissolving blood clots, and glucagon, which is used for treating hypoglycemia, are stable only in dry powder forms. Papaverine, which is optimally stored in solution at very acidic pH levels (in the range 2.0–2.8) must be mixed with a physiologically acceptable solvent immediately prior to injection to avoid the painful and destructive effects associated with acidic solutions. Other medically active substances which do not store well in forms which can be easily administered are adenosine triphosphate (available from Genentech) and Prostaglandin-E which has a shelf life of only 24 hours when mixed for infusion.

However, storage of a medically active substance in a stable non-injectable form necessitates the pre-injection mixing of the substance with a medically acceptable solvent. Therefore, separate containers for solvent and solute are generally used. However, this method of pre-injection mixing is inconvenient because it requires more than one container. The use of more than one container is also undesirable because judgement on the part of the person mixing the medication is required to use amounts which result in an appropriate dosage and also because of the problems surrounding the difficulties in maintaining sterility when materials from two or more separate containers are mixed.

Thus, it can be seen that a need exists for injection devices which increase the shelf-life of particular pharmaceuticals by separately storing the various components of certain medicaments for a commercially acceptable period of time until a time just prior to injection. A related need is for devices which increase those shelf-lives and which require a minimum of preparation to insure a dependable and correct dosage administration. The fulfillment of such need will permit the commercial availability of many pharmaceuticals which have been heretofore available only directly from professional medical personnel.

In an attempt to solve these problems, a number of wet-dry syringes which incorporate both solvent and medically active solute in the same cartridge to be mixed just prior to injection have been developed. U.S. Pat. No. 4,689,042 to Sarnoff et al. shows a two-barreled syringe wherein the solid medicament and liquid solvent are stored in separate container portions of the device. Pre-injection mixing and injection in Sarnoff are controlled by a number of biasing springs which sequentially operate by way of releasing mechanisms to propel the solvent from one compartment into a dry medicament-containing compartment via communicating passages. The entire apparatus is then agitated by the operator to mix the medicament and solvent prior to the injection. The operator then places the injection needle into target tissue and actuates an injection mechanism which propels the mixed medicament into the subject. Sarnoff is a complex mechanism employing many components and requiring several discrete operating steps to use.

Similarly, U.S. Pat. No. 4,755,169, also to Sarnoff et al. discloses a multi-compartmented stacked syringe-within-a-syringe assembly wherein a biasing spring propels a mixing/injection piston and primary needle to rupture a seal between the respective medicament component compartments of the device. After agitation of the device and insertion of the injection needle into a target site by the operator, the biasing spring is again actuated to drive a second piston which propels the mixed medicament into the subject. Although somewhat simpler than the device of the '042 Sarnoff patent, the invention of the '169 patent is also a complex mechanism employing many components and requiring several discrete operating steps to use.

U.S. Pat. No. 4,328,802 to Curley et al. discloses a wet-dry syringe and connected vial which are separated during use and wherein the piston portion of the syringe, being biased by a spring, is actuated to inject the solvent into the solute vial whereby mixing occurs. Manual aspiration into the syringe is then necessitated to charge the syringe with the mixed medicament/solvent solution. Removal of the syringe portion from the syringe/vial assembly is required prior to injection into the subject.

Other two-chambered syringes are marketed under the tradename Variject, manufactured by Bunder Glas GmbH. The Bunder device is a single cylinder syringe wherein a fluid bypass allows mixing of the medicament solvent and medicament during operation of the device.

The multiple piston assemblies of the aforementioned devices are mechanically complex and expensive to manufacture. In addition, none of the aforementioned devices provides for the withdrawal of the used injection needle to reside completely within the device to afford safe disposal and disease prevention characteristics.

Another problem in the medical field is that of the communication of infectious diseases caused by used needles and syringes and fluids therefrom coming into contact with doctors, nurses, or other medical personnel. Needle tips often remain exposed after aspiration of a fluid or blood from a subject, or after injection of a medicine into a subject and medical personnel are sometimes accidentally pricked with such tips. This problem is particularly acute in situations where a syringe and needle have been contaminated with particularly virulent organisms such as the AIDS virus or the hepatitis virus. The risk of puncture with a contaminated needle point is of particular concern after an injection because a finger, hand or other part of the person administering the injection is typically in close physical proximity to the needle during its removal from the subject's tissue, during replacement of a needle or the needle cover or during removal of the needle from a syringe for disposal.

There is also danger of such exposures to personnel, such as maintenance people, other than medical personnel, when a used needle and/or syringe is laid aside or discarded with a needle tip still exposed. This danger continues even when a used needle and/or syringe are placed in a disposal container. For instance, it is a routine medical procedure to use a device which cuts off the tip of an exposed needle so that it may not be re-used. However, this procedure still leaves exposed needle stubs and syringe parts which may be contaminated with infectious agents and with which persons may come into contact and be infected. Thus, it is not uncommon for discarded needle stubs to protrude through plastic garbage bags or other containers and present serious risk of a puncture wound to a person handling or otherwise coming into contact with the container. Similarly, even after used needles are removed from syringes and placed in sealed containers, the exposed syringes must also be placed in sealed containers to reduce the likelihood of infectious contact with personnel. Sanitary disposal of used needles and used syringes is an expensive and time consuming process and entails significant risk of exposure to infectious disease vectors.

A related problem is that of the dangers of exposing a needle to the atmosphere prior to its being used in giving an injection or withdrawing a body fluid. Not only is there danger of wounds to user personnel and patients from the exposed needle tip, but also there is the danger that the exposed needle will become contaminated by airborne or aerosol borne microbial and other contaminants and infect the patient eventually injected. This danger is particularly acute in hospitals and other medical treatment areas where strains of antibiotic resistant microbes endemically contaminate the air and all exposed surfaces. Contact with non-sterile air is a certainty with conventional exposed needle syringe technology because, in this technology, needles are routinely exposed to the air or surfaces for some discrete amount of time during use. Also, in emergency use situations such as military combat, natural disasters, or industrial accidents, the unused needle may be left exposed to such contaminants by untrained, harried or inexperienced personnel.

An additional problem in the field is that of dosage management. For subjects who give themselves injections, either because they require regular doses of injected pharmaceuticals or because medical personnel are not available, it is critical to insure that dosages are correct. Diabetic subjects often find themselves in such situations, particularly diabetics who suffer from the related condition of blindness. Other blind people are similarly in need of a product which insures that both the type of medication and its dosage are correct for their specific needs. Similarly, soldiers in the field, travelers requiring regular injectable medications, and subjects in emergency situations where self-injection is necessary often have difficulty administering the proper dosage of a given drug and often have difficulty in using a conventional syringe. Such problems are also compounded by darkness or poor lighting conditions in battlefield, power failure, and other crisis or emergency situations.

Thus, it can be clearly seen that there is a need for injection devices which contain pre-measured dosages of particular pharmaceutical substances wherein the administration or self-administration of those doses can be easily and dependably achieved by non-professional personnel.

SUMMARY OF THE INVENTION

It is an object of the present invention to provide a simplified syringe for the separate storage and pre-injection mixing of a medically active substance and a physiologically acceptable solvent or fluid.

Another object of the present invention is to provide a disposable safety syringe adapted to be used manually or with an automatic injector for the separate storage and pre-injection mixing of a medically active substance and a physiologically acceptable solvent or fluid.

It is a similar object of the present invention to provide a syringe adapted for the pre-injection mixing of at least one liquid component with another component which has the safety feature of an injection needle which withdraws after use to reside completely within the closed cartridge, thus reducing the dangers of infection or injury resulting from accidental contact with exposed needles.

It is an additional object of the present invention to provide a cartridge syringe with means for automatically mixing medicament components immediately prior to injection.

It is also an object of the present invention to provide concealment of an injection needle at all stages of use, thereby reducing the apprehension of the patient.

It is similarly an object of the present invention to maintain sterility of an injection needle at all stages of use by providing means whereby the needle, prior to contact with the skin of a patient for penetration therethrough, is never exposed to any potentially contaminating surfaces, aerosols or airborne particles or microbes.

It is still another object of the present invention to provide a sanitarily disposable injection vial with a needle which, after use in an injection, retracts completely into said vial to reduce the risk of disease transmission caused by the risk of exposure to a contaminated needle or to a contaminated syringe or to parts thereof.

It is yet another object of the present invention to provide a sanitarily disposable injection vial which can be safely discarded without the need for special equipment or containers and which can be safely and sanitarily disposed of in non-hospital, rugged, or emergency environments.

It is also an object of the present invention to provide a cartridge syringe for dispensing medication which can be filled by the use of conventional pharmaceutical packaging machinery, thus avoiding the substantial expense which would be required for the development and production of non-conventional packaging methods and machinery.

It is also an object of the present invention to reduce the risk that an incorrect dosage of a fluid medicine will be administered by injection.

It is an additional object of the invention to provide a needle assembly housing which can be used with necked medicament containers.

In accordance with the objects of the invention, a mixing syringe for two-component medicaments is provided. The mixing syringe has a cartridge housing having a first end and a second end, a substantially cylindrical cartridge housing bore, a slidable cartridge disposed in the cartridge housing bore having a first end, a second end, and a temporary sealing barrier disposed between the first and second ends separating the bore of the cartridge into a cylindrical medicament solvent charge chamber and a cylindrical medicament charge chamber.

The cartridge housing is also provided with means, fixedly attached thereto, for breaching the temporary sealing barrier, the cartridge being suitable for separately storing a medicament solvent charge and a medicament charge in the medicament solvent charge chamber and the medicament charge chamber, respectively, the charges to be mixed to form a medicament to be expelled from the cartridge.

A piston is disposed within the first end of the cartridge and is slidably seated in the cartridge bore. A retractable needle housing assembly is slidably disposed in the cartridge housing and a retractable injection needle is provided fixedly attached to the needle housing assembly and extending therethrough for injecting mixed medicament. A puncturable cartridge end stopper is provided rigidly attached to and sealing the second end of the cartridge. In some embodiments of the invention, a puncturable end cap, the end cap sealing the second end of the cartridge housing and having a needle guide disposed therein is provided.

Further in accordance with the objects of the invention, an operating shaft for operating the piston and the cartridge and for adapting the cartridge to other devices is provided in the piston. The operating shaft may be provided with a chamber for receiving a pushrod or injection needle portion which has punctured the piston therethrough. In some embodiments of the invention, the breachable temporary sealing barrier is so configured that the piston can pass sealably therethrough after the barrier is breached. In accordance with this aspect of the invention, various valves, having substantially cylindrical openings which permit the piston of the cartridge to pass therethrough, are provided. These valves include but are not limited to stopcocks, membranes and seats therefor, iris valves, and ball and seat valves.

In accordance with additional objects of the invention, a needle housing assembly for use with necked medicament containers which have puncturable end stoppers is provided. The assembly is provided with a needle housing, locking means disposed in the needle housing for locking the housing to the necked medicament container when the needle housing assembly and the necked cartridge become a predetermined distance apart upon relative movement between the necked medicament container and the needle housing, and an injection needle.

The injection needle is provided with a hollow shaft, an internal end, an internal shaft portion, an external end, an external shaft portion, first and second apertures, and a passageway extending through the hollow shaft and connecting the first and second apertures, the needle being rigidly attached to and extending through the needle housing, the internal end and internal shaft portion of the needle being adapted to puncture a necked medicament container, and the external end and external shaft portion of the needle being adapted to expel a medicament out of the needle housing assembly.

The means for locking the housing to a necked medicament container comprises protrusions which are disposed in the housing and which are adapted to securely engage the neck and head portions of a medicament container. In a preferred embodiment, the needle assembly housing is provided with flanges which are disposed to capture and securely hold the neck and end portions of a necked medicament container.

The needle assembly housing of the present invention is adapted to be used within a cartridge housing having an expansion chamber which permits expansion of the needle assembly housing flanges in conjunction with a slidable cartridge for the capture thereof but can also be used independently with various necked medicament containers which are not used with a housing.

In accordance with yet other embodiments of the invention, the means fixedly attached to the cartridge housing for breaching a temporary sealing barrier between chambers of said slidable cartridge comprises a spiral pushrod having an anchoring end and a puncturing end suitable for engaging the operating slot of a rotor valve, the anchoring end being provided fixedly attached to the cartridge housing and the spiral pushrod extending from the cartridge housing toward the cartridge puncturable end stopper, through a pushrod aperture provided in a needle assembly housing for freely guiding the pushrod therethrough so that the puncturing end of the pushrod resides in close proximity to and in alignment with the puncturable cartridge end stopper. In an additional embodiment of the invention, the spiral pushrod is adapted to operate a mixing rotor provided in the cartridge for agitating the solvent/solute mixture as it passes through the cartridge to be expelled therefrom.

In accordance with still further objects of the invention, a mixing syringe for two-component medicaments is provided comprising a cartridge housing having a first end and a second end, the cartridge housing having a substantially cylindrical cartridge housing bore, a slidable cartridge disposed in the cartridge housing bore and having a first end, a second end, and a temporary sealing barrier disposed between the first and second ends and separating a cartridge bore of the cartridge into a cylindrical medicament solvent charge chamber and a cylindrical medicament charge chamber, the cartridge housing having means, fixedly attached thereto, for breaching the temporary sealing barrier, and being suitable for separately storing a medicament solvent charge and a medicament charge in the medicament solvent charge chamber and the medicament charge chamber, respectively, the charges to be mixed to form a medicament to be expelled from the cartridge.

The cartridge is also provided with a piston disposed within the first end of the cartridge and being slidably seated in the cartridge bore, and a needle housing assembly rigidly attached to the cartridge and contained wholly within the cartridge housing. Also provided is an injection needle which is containable wholly within the cartridge housing, which can be extended to a position in which at least a portion of the needle extends outside of the cartridge housing, the needle being fixedly attached to the needle housing assembly and extending therethrough for injecting mixed medicament. The cartridge is also provided with a puncturable end cap, the end cap sealing the second end of the cartridge housing, and means for retracting the needle to reside completely within the cartridge housing after the expulsion of the medicament from the syringe is completed. The breachable temporary sealing barrier is so configured that the piston can pass sealably therethrough after the barrier is breached being provided with a cylindrical bore of substantially equal dimension to that of the cartridge bore so that the piston can pass sealably therethrough after the barrier is breached. The barrier can be a valve disposed through the cartridge having an operating cam disposed on the exterior of the cartridge wherein the valve operating cam is configured to be operated by a pushrod integral to the cartridge housing.

Yet further in accordance with the objects of the invention are provided an electronically or magnetically actuated pushrod contained within the cartridge and an electronic or magnetic pushrod actuator contained within the cartridge housing for breaching the temporary seal between chambers of the slidable cartridge.

Yet still further in accordance with additional objects of the invention, a mixing syringe is provided for the pre-injection mixing of two-component medicaments which comprises a cartridge housing having a first end and a second end, the cartridge housing having a substantially cylindrical cartridge housing bore and a slidable cartridge disposed in the cartridge housing bore having a first end, a second end, and a temporary sealing barrier disposed between the first and second ends and separating the cartridge bore into a cylindrical medicament solvent charge chamber and a cylindrical medicament charge chamber, the cartridge being suitable for separately storing a medicament solvent charge and a medicament charge in the medicament solvent charge chamber and the medicament charge chamber, respectively, the charges to be mixed to form a medicament to be expelled from the cartridge. The cartridge is provided with a piston disposed within the first end of the cartridge and being slidably seated in the cartridge bore and a retractable needle housing assembly slidable in the cartridge housing the needle housing having means, fixedly attached thereto, for breaching the temporary sealing barrier. The device is further provided with a retractable injection needle having a hollow shaft, an internal end, an internal shaft portion, an external end, an external shaft portion, first and second apertures, and a passageway extending through the hollow shaft and connecting the first and second apertures. The needle is rigidly attached to and extends through the needle housing, the internal end and internal shaft portion of the needle being adapted to puncture the cartridge, and the external end and external shaft portion of the needle being adapted to expel a medicament out of the needle housing assembly, the first injection needle aperture being disposed in the internal needle shaft portion an appropriate distance from the housing to receive fluid from a punctured medicament cartridge, and the second injection needle aperture being disposed in the external needle end.

BRIEF DESCRIPTION OF THE DRAWINGS

FIGS. 2(a)-2(d) are sectional elevation views of a cartridge syringe constructed in accordance with a second embodiment of the present invention which utilizes a burstable membrane as a means for separating the chambers of the cartridge and which utilizes an elution column for storage of the medicament solute.

FIGS. 3(a)-3(d) are sectional elevation views of a cartridge syringe constructed in accordance with another embodiment of the present invention wherein the means for separating the chambers of the invention is a rotary valve operated by a spiral twist rod.

FIGS. 6(a)-6(c) are sectional elevation views of a cartridge syringe constructed in accordance with yet another embodiment of the present invention wherein a burstable membrane barrier is breached by an electronically or magnetically activated means and wherein the injection needle is fixedly attached to the cartridge.

FIG. 9(a) is a sectional elevation view of a cartridge syringe constructed in accordance with the present invention similar to that shown in FIGS. 5(a)-(f) but wherein a spherical ball valve having an aperture suitably configured for the passage therethrough of the piston and a solute is disposed on a grid in the necked portion to permit substantially complete evacuation of the cartridge are provided.

FIG. 9(b) is a detail view of the ball valve operating cam in the closed position of FIG. 9(a).

DETAILED DESCRIPTION OF THE PREFERRED EMBODIMENTS

Figure 1:
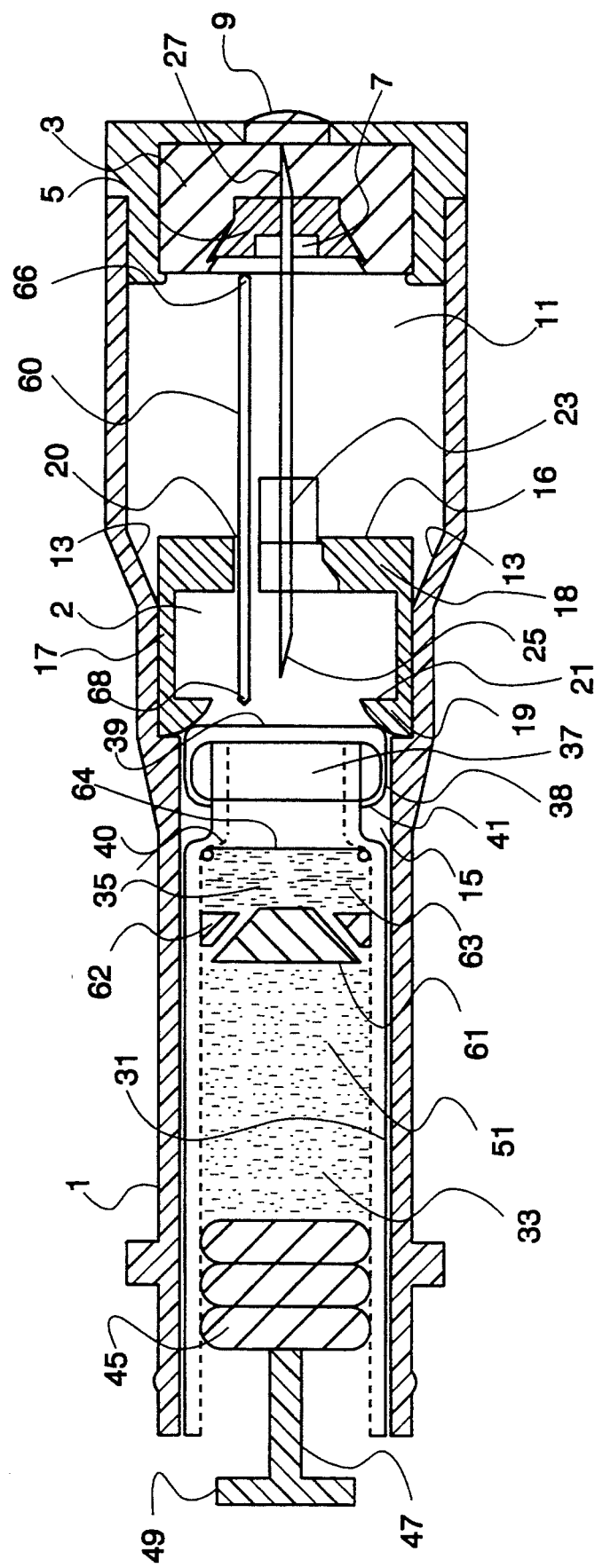
FIG. 1 is a sectional elevation view of a cartridge syringe constructed in accordance with a first embodiment of the present invention which utilizes a plug as a means for separating the chambers of the cartridge.

The advantages and characteristics of the cartridge mixing syringe and needle housing of the present invention can be elucidated from the following detailed description of several embodiments of the mixing syringe and needle assembly to be taken as examples and not as limitations in conjunction with the accompanying drawings.

From the information herein, it is also clear that many permutations of the present invention other than those shown in the drawings are possible by the combination of components from the various embodiments. For example the needle assembly housing and cartridge housing shown in FIG. 2 could, with slight modification, be adapted to utilize the magnetically or electronically actuated burstable membrane components shown in FIG. 6.

With reference to FIG. 1, a two-component cartridge mixing syringe comprises a double ended circularly cylindrical cartridge housing 1 constructed of a rigid material such as polyethylene and having a cartridge residence chamber 15 and a needle housing residence chamber 2 and needle housing assembly receiving chamber 11. Cartridge housing 1 is provided with a puncturable sealing end cap 3 of resilient material such as butyl rubber, a plastic needle guide 5 rigidly embedded in end cap 3 and having a needle guide aperture 7 formed therein and an injection device positioning projection 9. End cap 3 is also provided with a pushrod 60 anchored to needle guide 5 at pushrod anchoring end 66 and constructed of a suitable material such as stainless steel. Pushrod 60 extends through a needle assembly housing pushrod aperture 20 toward a puncturable cartridge end stopper 39. Needle housing assembly receiving chamber 11 is further provided with curved abutments 13 of appropriate configuration to allow a needle assembly housing 18 to both enter and withdraw from needle assembly housing receiving chamber 11. Needle assembly housing 18 and a cylindrical cartridge 31 are initially disposed within needle housing residence chamber 2 and cartridge residence chamber 15, respectively.

Cylindrical cartridge 31 is constructed of a rigid material such as Lexan plastic, is slidably positioned within cartridge housing 1 and is provided with a three-portion chamber in which is stored a solvent charge 51 and a solute charge 63. Solvent charge 51 is stored in a first portion 33 of cartridge 31. Solvent charge 51 can consist of a single solvent or diluent, mixed solvents or diluents, a concentrated solution or one or more parts of a multiple-part medically active substance or system. First portion 33 is separated from a second cartridge solute storage portion 35 by a plug seat 62 which is rigidly affixed to the internal walls of cartridge 31 and a plug 61.

Second cartridge solute storage portion 35 has stored therein solute charge 63 in finely divided form on a puncturable high-surface-area solute trait grid 64. Solute charge 63 can consist of solid medicament, liquid medicament, a diluent for a concentrated solvent or one or more parts of a multiple-part substance or system. Solute charge 63 is disposed across second cartridge solute storage portion 35 so that solvent charge 51 moves through grid 64 thus dissolving solute charge 63 before the mixed solute/solvent is expelled through a hollow injection needle 23. A third cartridge injection needle portion 37 is provided with a puncturable cartridge end stopper 39 of a resilient material within a cartridge cap 38. A cartridge piston chamber abutment 40 forms a transition between second cartridge storage portion 35 and third cartridge injection needle portion 37 and forms a seat for solute tray grid 64. The external portion of the transition between third cartridge portion 37 and cartridge cap 38 forms a cartridge shoulder 41. Cartridge shoulder 41 functions as a flange engaging step for engaging flanges 19 of needle assembly housing 18 during operation of the invention.

Cartridge 31 is further provided with a piston 45 of a resilient material and having a piston shaft 47 and a piston shaft head 49 for reversibly engaging an injection/aspiration device or an adapter for manual operation. Such a cartridge could be engaged to an injection/aspiration device or manual adapter by any other means, other than a piston similar to piston 45 as shown, such as a T-shaft and keyway, a threaded rod, piston engaging barbs, or other means providing secure engagement of a cartridge to an injection/aspiration device. It is preferred that the means for engaging be reversible.

Needle assembly housing 18 is of a rigid material such as linear polypropylene and is provided with a needle assembly housing bottom 16, needle housing walls 17, needle assembly housing flanges 19 and needle assembly housing lips 21 disposed for securely engaging cartridge 31. Needle assembly housing 18 is also provided with a needle assembly housing pushrod aperture 20 having sharpened stainless steel pushrod 60 passing therethrough. Needle assembly housing 18 is further provided with the hollow injection needle 23 which is rigidly attached to housing 18 and which passes therethrough. Injection needle 23 has an internal tip 25 disposed toward puncturable cartridge stopper 39 and an external tip 27 for selective movement out of the housing and insertion into target tissue which passes through aperture 7 of needle guide 5 but does not protrude through sealing end cap 3 until operation of the invention.

The relative lengths of needle assembly housing walls 17, needle assembly housing receiving chamber 11, and pushrod 60 are such that, in operation of the device as described hereinbelow, a pushrod puncturing end 68 of pushrod 60 penetrates puncturable cartridge end stopper 39 and dislodges plug 61 from plug seat 62 before needle internal tip 25 contacts puncturable cartridge end stopper 39. Third cartridge injection needle portion 37 is captured by the engagement of needle assembly housing flange lips 21 by cartridge shoulder 41 of cartridge 31 when cartridge 31 has been propelled a sufficient distance toward puncturable cartridge sealing end cap 3 so that needle assembly housing 18 is fully within needle assembly housing receiving chamber 11.

The above-described embodiment of the mixing syringe operates as described hereinbelow.

Piston 45 is propelled toward sealable end cap 3 by the application of force to plunger shaft head 49 in the direction of sealing end cap 3, which force is communicated through plunger shaft 47 to piston 45 thus applying hydraulic pressure through solvent charge 51, plug 61 and plug seat 62, and forcing cartridge 31 and needle assembly housing 18 having injection needle 23 fixedly attached therethrough toward sealing end cap 3, this action simultaneously forces cartridge 31 onto pushrod end 68, which slides freely through needle assembly housing pushrod aperture 20, thus also propelling injection needle 23 through needle guide aperture 7 causing external needle tip 27 to puncture puncturable sealing end cap 3. The relative lengths of needle assembly housing walls 17, needle assembly housing receiving chamber 11 and pushrod 60 are such that pushrod puncturing end 68 penetrates puncturable cartridge end stopper 39 and dislodges plug 61 from plug seat 62 thus causing solvent charge 51 to enter second cartridge solute storage portion 35 before injection needle internal tip 25 contacts puncturable cartridge end stopper 39 thereby allowing the mixing of solvent charge 51 and solute charge 63. By varying the rate at which cartridge 31 is propelled toward end cap 3 after pushrod 60 dislodges plug 61, and before internal injection needle tip 25 punctures puncturable end cap 39, the solvation time during which solvent charge 51 and solute 63 can be controlled.

Continued force toward puncturable cartridge sealing end cap 3 by piston 45 continues to propel needle 23 outward and into the target tissue until needle housing 18 is stopped by sealable end cap 3, thus positioning needle assembly housing 18 within needle assembly receiving chamber 11 which is of a larger diameter than cartridge residence chamber 15. The positioning of needle assembly housing 18 within needle assembly housing receiving chamber 11 allows flanges 19 and walls 17 of needle assembly 18 to expand to irreversibly and securely receive and capture third cartridge injection needle portion 37 of cartridge 31. Continued pressure in the same direction causes piston 45 to move toward puncturable cartridge end stopper 39 thus causing expulsion of the mixed solvent charge 51/solute 63 solution through hollow injection needle 23 into the target tissue.

After injection of the mixed solvent charge 51/solute 63 solution through hollow injection needle 23 into the target tissue, the direction of force on piston shaft head 49 is reversed, thus causing the withdrawal of irreversibly captured needle assembly housing 18 into cartridge housing 1 and the withdrawal of injection needle 23 from the target tissue so that injection needle external tip 27 resides completely within cartridge housing 1.

Piston 45, although slidably seated in the bore of cartridge 31, is of a slightly oversize diameter so that the frictional force required to withdraw piston 45 back through the bore of cartridge 31 is much greater than the force required to withdraw cartridge 31 which has been captured by needle assembly housing 18 having needle 23 attached therethrough from an injection site to reside wholly within cartridge housing 1.

Figure 2A:
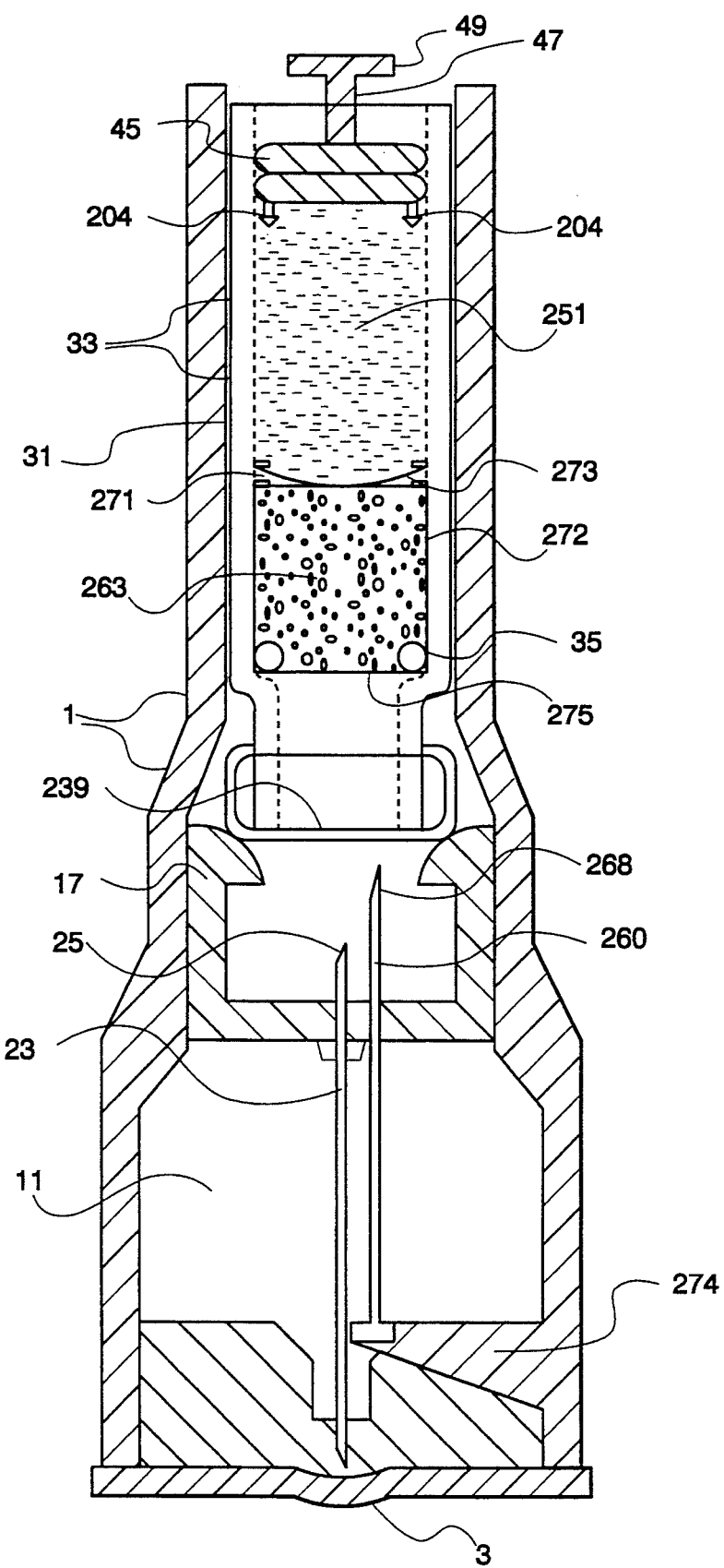

FIG. 2(a) shows an embodiment of the invention which differs from that shown in FIG. 1 by providing a burstable membrane as a barrier between the solvent and solute portions of the cartridge and by presenting the solute in an elutable bead column. With reference to FIG. 2(a), cylindrical cartridge 31 of rigid material such as water glass is slidably positioned within cartridge housing 1 and is provide with a three-portion chamber in which is stored solvent charge 251 and solute charge 263. Cartridge solvent portion 33 is separated from cartridge solute storage portion 35 by a membrane seat 271, a resilient circular U channel made from vulcanized rubber, which is rigidly attached and sealed to the internal walls of cartridge 31 either by pressure generated by oversizing the diameter of the wall adjacent to the cartridge wall or an industrial adhesive known to the art, into which is fitted a burstable membrane 273 of a material such as natural rubber or styrene film locked in by an O-ring [not shown].

Second solute storage portion 35 has stored therein a bead column 272 of ion exchange resins such as Rhom and Haas's Amberlite cationic or anionic resins. In this embodiment of the invention, the resins are saturated with the appropriate solute charge 263 and subsequently eluted by solvent charge 251. It should be noted that in most instances the critical factor in drug delivery is the dosage amount of solute charge 263 while a surplus of solvent charge 251 is widely tolerated. Supporting the base of the bead column 272 is a puncturable permeable grid 275. Bead column 272 is charged into cartridge solute storage portion 35 so that in operation of the invention solvent charge 251 moves through bead column 272, dissolving solute charge 263 before being expelled through hollow injection needle 23.

The relative lengths of needle assembly housing walls 17, needle assembly receiving chamber 11 and pushrod 260 on shelf 274 are such that in operation of the device as described hereinbelow sharpened pushrod puncturing end 268 penetrates puncturable cartridge end stopper 239 and burstable membrane 273 before needle internal end 25 contacts puncturable end stopper 239. This can be best seen in FIG. 2(a). By controlling the length of time between which burstable membrane 273 is punctured by pushrod 260 and needle tip 25 punctures cartridge end stopper 239 the solvation time in which solvent 251 moves through solute 263 can be varied as needed for particular solute/solvent combinations.

The embodiment of the invention shown in FIGS. 2(a)-2(e) operates in a similar manner to that described with reference to FIG. 1 above and is further illustrated in FIG. 2(b)-2(e) showing the device in four positions of the injection/retraction cycle. FIG. 2(b) shows the invention in its initial storage position.

FIG. 2(c) shows the invention after force has been applied to piston 45 through shaft head 49 of shaft 47, forcing cartridge 31 and needle assembly housing 18 having injection needle 23 rigidly disposed therethrough toward puncturable cartridge housing sealing end cap 3 sufficiently far so that pushrod 260 has punctured cartridge end stopper 239, grid 275, and burstable membrane 273 and has expanded the flanges of needle assembly housing 18 which, in this position, is shown bottomed out in needle assembly housing residence chamber 1 but has not yet been propelled sufficiently far that the internal end of needle 23 has punctured puncturable cartridge end stopper 239. FIG. 2(c) thus shows the device in a position wherein solvent 251 is exposed to solute 263 but does not yet have an avenue through injection needle 23 for expulsion from cartridge 31.

FIG. 2(d) shows the device after cartridge 31 has been further propelled toward sealing end cap 3 a sufficient distance so that the flanges of needle assembly housing 18 have irreversibly captured the cap and neck portion of cartridge 31 and piston 45 has propelled part of the solvent charge 251 through solute 263 and into the third portion of the chamber of cartridge 31 for injection.

Although not shown, it is obvious that continued force on piston 45 propels an additional amount of solvent 251 through solute 263 to inject the required amount of the medicament whereupon barbs 204 irreversibly engage membrane seat 271 so that reversal of the force on piston 45 withdraws cartridge 31 needle assembly housing 18 and injection needle 23 to fully reside within cartridge housing 1 after the injection has occurred. FIG. 2(e) shows the fully withdrawn cartridge with attached needle assembly housing and needle. Rigidly anchored into rubber plunger 45 are stainless steel barbs 204.

Figure 3A:
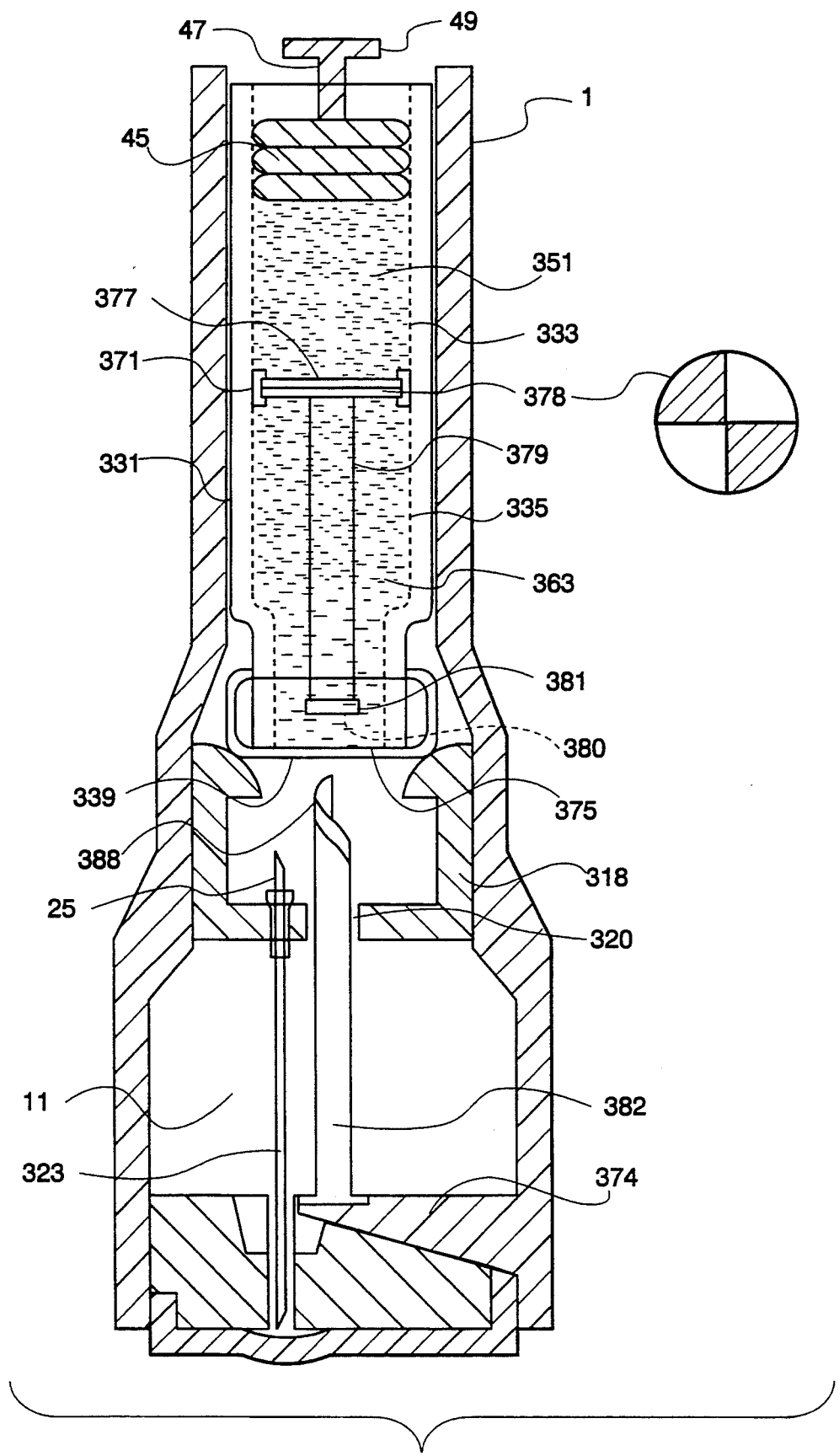

FIG. 3 shows an embodiment of the cartridge of the present invention having liquid constituents in both upper and lower portions of the cartridge. This embodiment is known as a wet/wet cartridge. The temporary barrier device for separating the portions of the cartridge is a rotatable disk assembly valve separation barrier and trigger therefor that extends the time available for mixing. FIGS. 3(a), 3(b), 3(c) and 3(d) show three operating positions of the device.

With reference to FIG. 3, cylindrical cartridge housing 1 is fitted with a shelf 374 that is integral with cylindrical cartridge housing 1 into which is imbedded a rigid rectangular spiral pushrod 382 coaxially aligned with cylindrical cartridge 31. An injection needle 323 is sufficiently offset in needle assembly housing 318 so as not to interfere with the operation of rectangular spiral pushrod 382. Cylindrical cartridge 331 is slidably positioned within cartridge housing 1 and is provided with two chambers in which are stored a solvent charge 351 and a solution charge 363. Solvent charge 351, such as Prostaglandin E, available from Upjohn Pharmaceutical, a vasodilator that is provided in a solution of absolute alcohol and must be diluted with sterile water before injecting, is stored in first portion 333 of cartridge 31 and solution charge 363, such as the diluent distilled water, is stored in second cartridge portion 335. First cartridge solvent portion 333 is separated from second cartridge solution storage portion 335 by a disk assembly valve comprising double disk valve seat 371, a circular stator disk 377, and a circular rotor disk 378. Double disk valve seat 371, a resilient circular U channel made from castable silicone rubber, is rigidly attached to the internal walls of cartridge 331 either by pressure generated by oversizing the diameter of the wall adjacent to the cartridge wall or an industrial adhesive known in the art, into which is permanently fitted circular stator disk 377, made from rigid rubber with alternate quarters open and circular rotor disk 378, made from stainless steel with alternate quarters open, which is free to rotate in double disk valve seat 371. The disks are arranged so that the open quarters do not overlap thus leaving the disk assembly valve closed. This arrangement can be seen in FIG. 3(a). Rigidly attached to circular rotor disk 378 by rods 379 is a driven slotted member 381. Driven slotted member 381 has a rectangular slot 380 of an appropriate dimension so that a rectangular spiral pushrod 382 will cause driven slotted member 381 to rotate as it follows the spiral of spiral rod 382. The sharpened spiral tip 388 of rectangular spiral pushrod 382 is of a thickness, length and rotation to cause driven slotted member 381 to rotate 90 degrees and pierce cartridge end seal 339 without causing leakage therefrom.

The above described embodiment of the wet/wet cartridge syringe operates as described below.

Piston 45 is propelled towards end cap 3 by the application of force to plunger shaft head 49 in the direction of end cap 3 which force is communicated through plunger shaft 47 to piston 45 thus applying hydraulic pressure through solvent charge 351 disk assembly valve rotor 378 and stator 377 thus forcing cartridge 31 and needle assembly housing 318 having injection needle 323 fixedly attached therethrough towards end cap 3 simultaneously forcing cartridge 31 onto sharpened tip 388 of rectangular spiral pushrod 382 which slides freely through needle assembly housing aperture 320 thus also propelling injection needle 323 to puncture end cap 3 and thin wall 375. When the tip 388 of rectangular spiral pushrod 382 passes through rectangular slot 380 so that driven slotted member 381 turns as it follows the spiral curve of spiral tip 388. Rigid rods 379 cause circular rotor disk 378 to rotate 90 degrees, thus opening the disk assembly valve. This is illustrated in FIGS. 3(b) and 3(c). It is clearly seen that the disk assembly valve opens as soon as spiral tip enters into slot 380 at the beginning of the injection cycle, allowing solution charge 363 and solvent charge 351 time to mix before internal injection needle tip 25 punctures puncturable cartridge end stopper 339. End stopper 339 is punctured near the end of the injection cycle. See FIG. 3(c). The remainder of rectangular spiral pushrod 382 is linear so that no further rotation of valve rotor 378 occurs fixing the valve in an open position.

Figure 4:
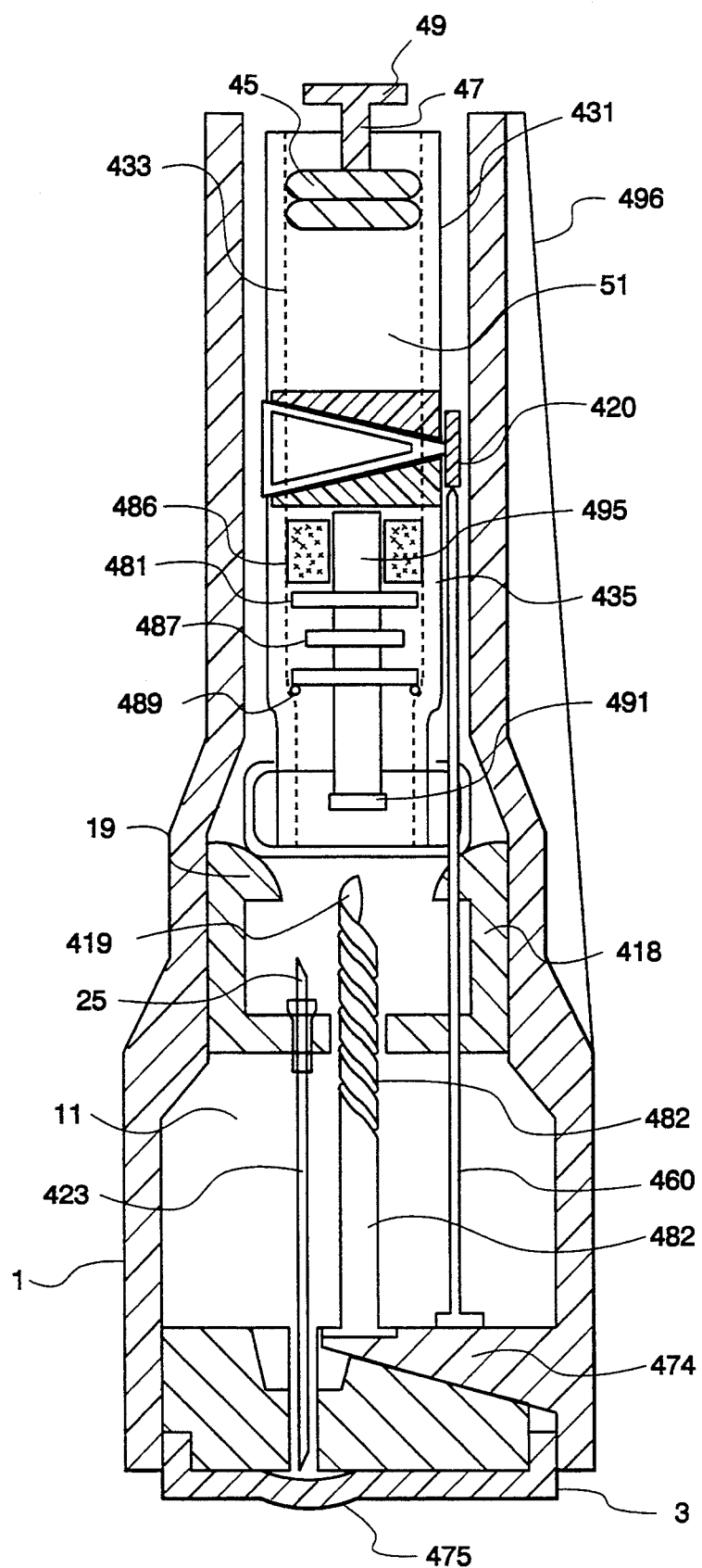
FIGS. 4 and 4(a)-4(c) are sectional elevation views of a cartridge syringe constructed in accordance with another embodiment of the present invention wherein the means for separating the chambers is a stopcock extending through the cartridge which is actuated by a pushrod and wherein means for automatically agitating the components of the medicament during operation is provided.

FIG. 4 shows a detailed view of one embodiment of the invention providing a stopcock as a temporary barrier between chambers of the cartridge. The stopcock is provided with an operating cam which is actuated by a pushrod disposed between the external surface of the cartridge and the internal surface of the cartridge housing. This embodiment is also provided with independently actuated means for automatically agitating the mixing solvent and solute charges during the injection cycle of the invention.

With reference to FIG. 4, cylindrical cartridge housing 1 is provided with a base shelf 474 that is integral with cylindrical cartridge housing 1 into which is imbedded a rigid rectangular spiral pushrod 482 formed from flat stainless steel and is disposed coaxially to cylindrical cartridge housing 1. Spiral pushrod 482 is provided with a sharpened spiral pushrod end 490. An injection needle 423 is offset in a needle assembly housing 418 to operate without interference from rectangular spiral pushrod 482. Needle assembly housing 1 is slidable in cartridge housing 1.

As in the embodiments shown in FIGS. 1, 2, 3, 4, and 7, cartridge housing 1 is provided with needle assembly housing residence chamber 1 of appropriate dimension to permit the expansion of needle assembly housing flanges 19 when needle assembly housing 418 resides wholly within chamber 11. Cylindrical cartridge 431 is slidably positioned within cartridge housing 1.

A first cartridge solvent reservoir portion 433 is separated from cartridge solute portion 435 by a stopcock assembly valve 420. Stopcock assembly valve 420 is made of materials known in the medical arts and can be of many different configurations such as those wherein the aperture of the valve is of an appropriate diameter to permit the cartridge piston to pass sealably therethrough. Additional embodiments of the stopcock assembly valve of the present invention are more fully elucidated in the description of FIG. 5 below.

With respect to FIG. 4, a valve operating pushrod 460 is shown fixedly attached to base shelf 474 and is freely disposed through an aperture (not shown) in needle assembly housing 418 for opening stopcock assembly valve 420 and is outside cartridge 431 leaving rectangular spiral pushrod 482 free to cause tube 491 to continually rotate and is fully described in FIG. 5. Fitted into the lower end of a tube 491 is driven spiral disk 481. Driven spiral disk 481 has an oval slot of a dimension so that the rectangular spiral pushrod 482 will cause driven spiral disk 481 to rotate as it follows the spiral pattern. Rigidly attached to tube 491 are agitating rotor blades 487 the lower one of which rests on a silicone ring 489 which acts as a bearing for the structure. A mesh annular frame 486 hangs over a tube top cap 495 that is closed and allows no solvent to enter tube 491. The spiral pattern on spiral pushrod 382 is of a length to cause driven spiral disk 481 to rotate during the entire downward cycle of the syringe.

The above described embodiment of the two-component syringe of the invention operates as described hereinbelow.

Figure 4C:
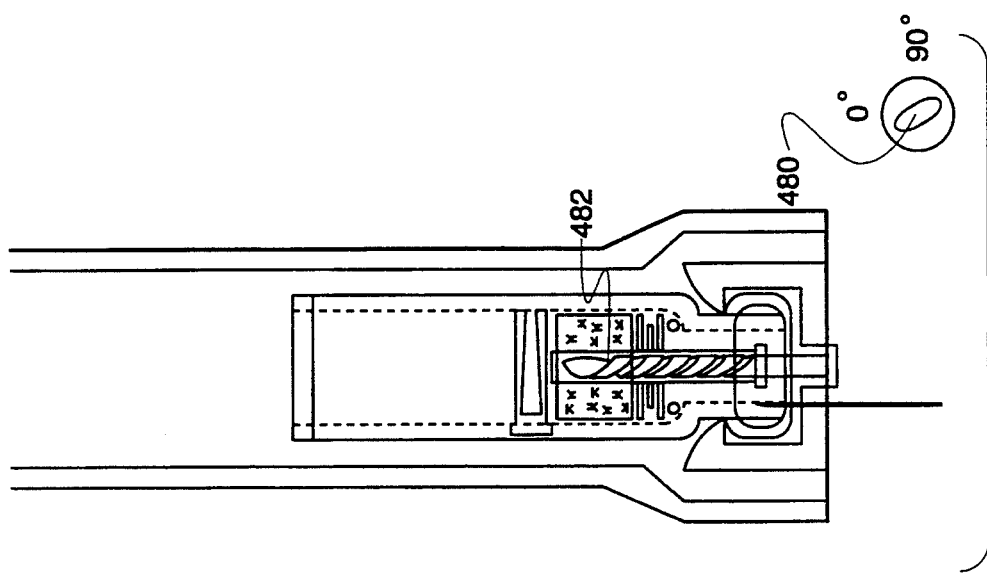
Figure 4B:
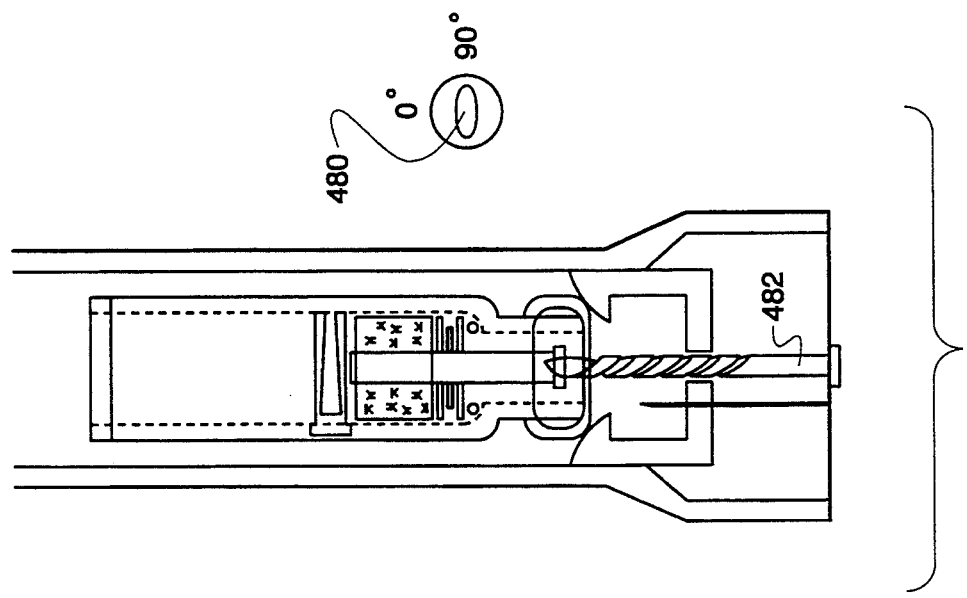
Figure 4A:
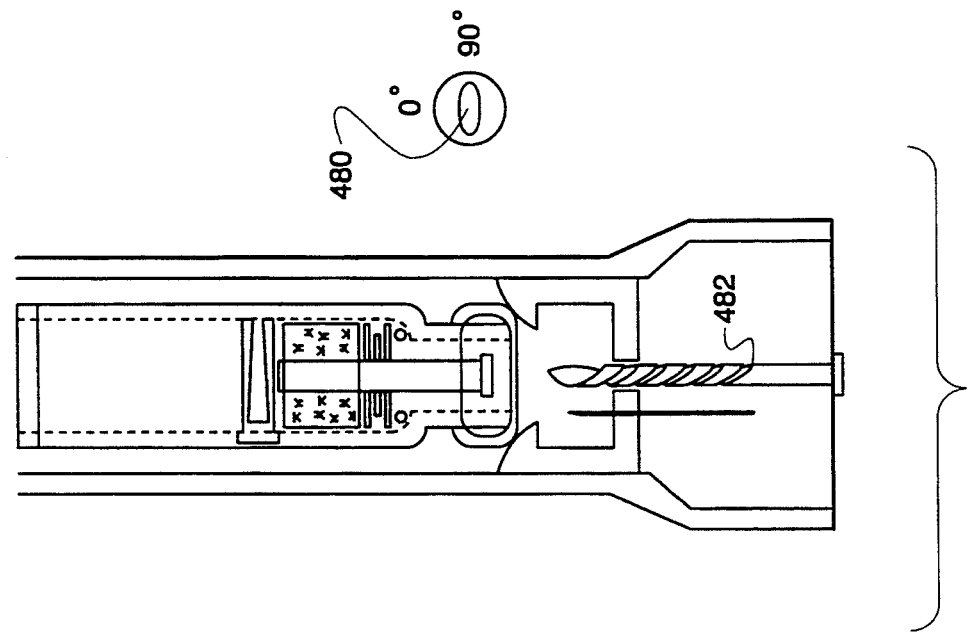

Piston 45 is propelled towards end cap 3 by the application of force to plunger shaft head 49 in the direction of end cap 3, which force is communicated through plunger shaft 47 to piston 45 thus applying hydraulic pressure through solvent charge 51 stopcock assembly valve 420 and forcing cartridge 431 and needle assembly housing 418 having injection needle 423 fixedly attached therethrough towards end cap 3 and simultaneously forcing cartridge 431 onto rectangular spiral pushrod 482 which slides freely through needle assembly housing aperture, thus also propelling injection needle 423 to puncture end cap 3 and thin wall 475. When the tip 490 of rectangular spiral pushrod 482 passes through oval slot 480, driven spiral disk 481 turns as it follows the spiral curve of shaft 482. Driven spiral disk 481 being rigidly attached to tube 491, will cause tube 491 to rotate continually, thus providing agitation to the mixing solvent and solute. This is most clearly seen in FIG. 4(b) and 4(c).

FIGS. 5 et. seq. illustrate an embodiment of the invention differing from the previously described embodiments by the provision of an elution maze for the solute and a stopcock disposed through the cartridge component of the invention and which is actuated by a set of ridges and grooves disposed within the cartridge housing. In a variation thereof, the stopcock can be configured to allow sealable passage therethrough.

FIGS. 5 (a), (b), (c), (d) and (e) show a two-component cartridge syringe of the present invention utilizing a two-chambered medicament cartridge slidable within a cartridge housing having an injection needle fixedly attached to the cartridge housing and an actuating ridge and groove integral with the cartridge housing for operating a stopcock and guiding and positioning the cartridge.

Figures 5A, 5B:
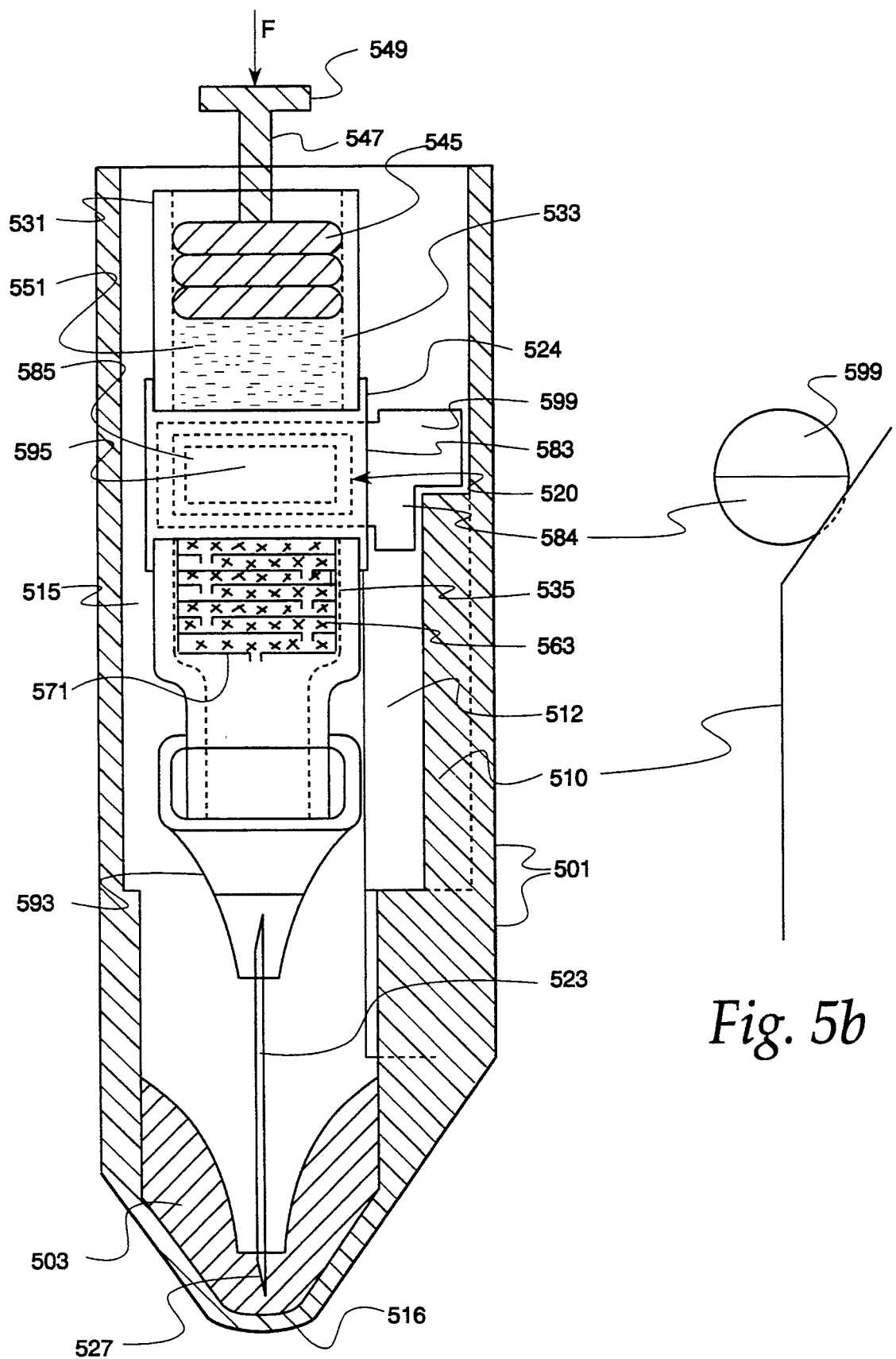
FIGS. 5(a)-5(e) are sectional elevation views of a cartridge syringe constructed in accordance with another embodiment of the present invention wherein a stopcock barrier means is actuated by a pushrod integral to the cartridge housing and wherein the medicament solute is disposed in a mixing maze through which the medicament solvent must flow.
Figure 5C:
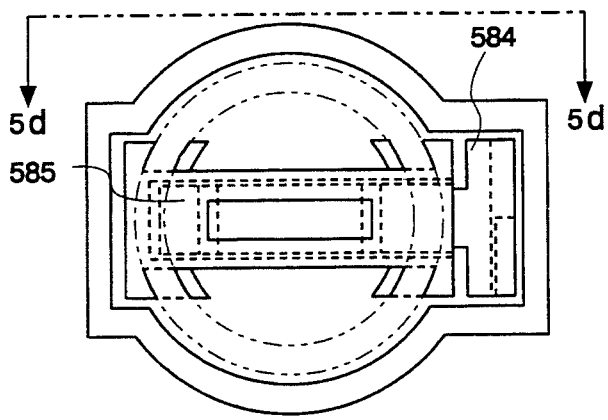
Figure 5D:
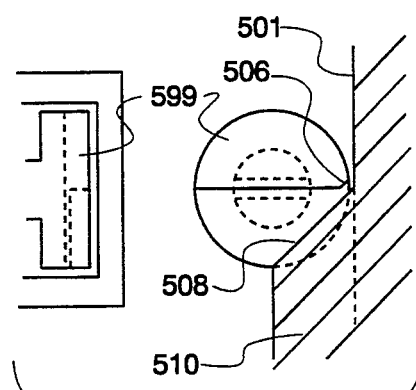
Figure 5F:
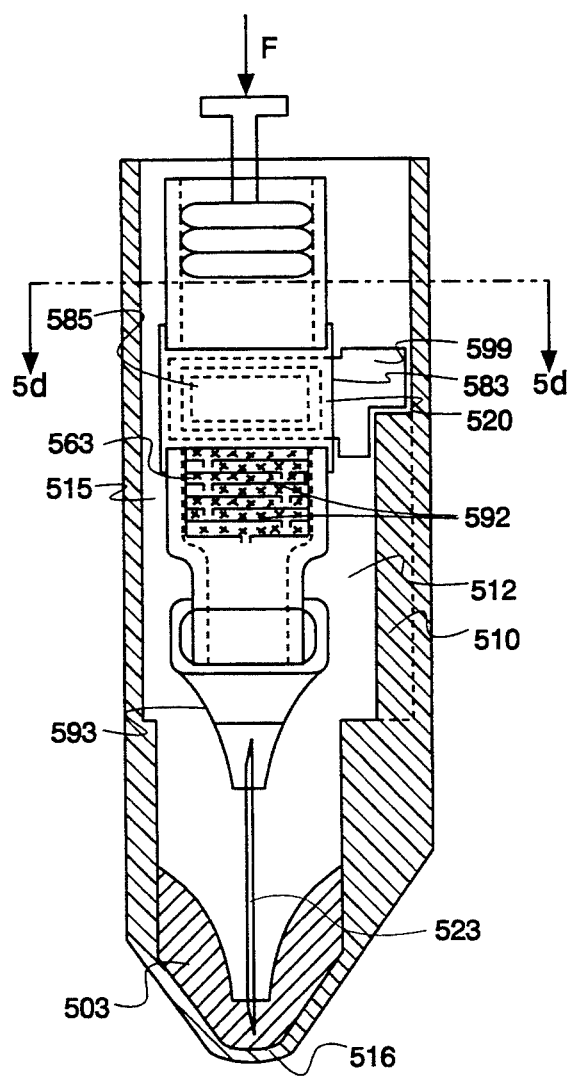
Figure 5E:
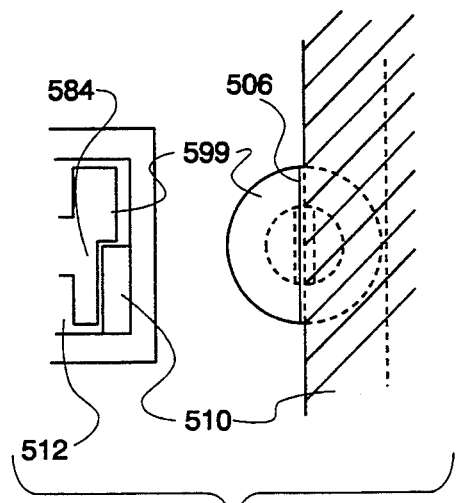

With reference to FIGS. 5(a), (b), (c), (d), and (e), a two-component cartridge syringe comprises a double ended substantially cylindrical cartridge housing 501 having an injection end and a cartridge operating end constructed of a rigid material suitable for injection molding such as linear polypropylene or polystyrene, and having a cartridge residence chamber 515 formed therein for slidably housing a two-chambered cartridge 531 and also having guide channel 512 and a channel ridge 510 positioned therein for operating and guiding a valve operating cam 584 and for engaging and rotating a cam protrusion 599 and valve rotor 583.

The injection end of cylindrical cartridge housing 501 wall 516 is significantly thinned in order to allow the injection tip and shaft of hollow injection needle 523 to puncture an end wall 516 thereof when cartridge 531 is driven toward puncturable end cap 503 that also functions as a shock absorber when cartridge 531 is driven toward it. End cap 503 is formulated, as is known in the art, of a resilient material that will not core out when a needle is embedded in it or when the needle moves therethrough at high speeds and will adsorb efficiently an energy shock as might be transmitted by an expanding spring One material having such properties and known in the art is chlorobutyl rubber. Cylindrical cartridge 531, constructed of a rigid material such as Pyrex glass, is slidably positioned within cartridge housing 501 and has two chambers in which are provided a solvent charge 551 and a solute charge 563. Solvent charge 551 is stored in a first portion 533 of cartridge 531 and solute charge 563 is stored in an elution maze 571 constructed and disposed in a second cartridge portion 535 in such a manner that solvent charge 551 is forced therethrough when a stopcock assembly 520 is actuated.

First cartridge portion 533 is separated from second portion 535 by stopcock assembly 520 comprising a cylindrical rotor housing/seal 585 made of a resilient material such as cast silicone rubber and provided with an aperture 595 that provides for the passage therethrough of solvent charge 551 into cartridge second portion 535 after cylindrical rotor housing/seal 585 is rotated by the relative movement of cartridge housing 501 with respect to cartridge 531 and the interaction of concentric cam 584 with guide channel 512 and channel ridge 510.

Cylindrical rotor housing/seal 585 and a valve rotor 583 are sealably fitted through valve rotor seats 524 disposed in the walls of cartridge 531. Rotor seats 524 and valve rotor 583 are preferably injection molded from a general purpose lubricating nylon polymer such as Zytel 101L.

Aperture 595 of cylindrical rotor housing/seal 585 causes the stopcock assembly to act as a valve. This can best be seen in FIG. 5(a). To the front end of cylindrical rotor cylinder 583 is attached the concentric cam 584 with a protruding hemisphere 599 which will cause the cylindrical rotor cylinder 583 to rotate 90 degrees when the cartridge 531 slides down the circular cylindrical cartridge housing past the channel ridge 510 and channel 512. This 90 degree rotation aligns the rotor aperture 595 with the cylinder bore allowing passage of solvent charge 551 into cylinder second portion 535. Second cartridge solute storage portion 535 has stored therein solute charge 563 in finely divided form on column trays 592 individually injection molded and sealably stacked to the desired height so that solvent charge 551 travels through one tray to the next before being expelled through hollow injection needle 523. Injection needle 523 made from hollow stainless steel tubing has an external tip 527 which does not protrude through sealing end cap 503.

The above described embodiment of the wet/dry, wet/wet syringe operated as described herein below.

Piston 545 is propelled towards sealable end cap 503 by the application of force to plunger shaft head 549 in the direction of end cap 503, which force is communicated through plunger shaft 547 to piston 545, thus applying hydraulic pressure through solvent charge 551 and stopcock assembly valve 520 and forcing cartridge 531 together with permanently attached needle assembly 593 towards end cap 503 causing cartridge 531 to slide down cartridge housing 501. As the hemispheric portion 599 of cam 584 which is perpendicular to channel ridge 510, slides down guide channel 512 its radius end 506 engages the 45 degree incline 508 at the top of channel ridge 510, starting cam 584 to rotate. This action is best seen in FIG. 5(a).

The cam 584 is attached to valve rotor 583 whose aperture 595 is in the horizontal (closed) attitude when the hemispheric portion 599 of cam 584 is in its horizontal (closed) attitude.

As the cam 584 slides down guide channel 512 the cam 584 rotates 90 degrees causing aperture 595 to assume a vertical (open) attitude (this action can best be seen in FIG. 5(b) thus lining up with the cartridge bore.

Continued movement by piston 545 toward end cap 503 propels needle 523 though puncturable cartridge end cap 503 and puncturable thin wall 516 into target tissue. The force needed to inject the needle into target tissue is in the order of 6 oz., while the backpressure needed to force the solvent charge 551 through the tray column is in the order of pounds. Therefore the open stopcock assembly value will continue to allow the force to be translated through the piston to the cartridge. Once the cartridge 531 is seated in the down position so that needle assembly 593 is contacting end cap 503, solvent charge 551 is forced through elution maze 571 thus eluting solute charge 563 therefrom and the mixed medicament is expelled through hollow injection needle 523 into target tissue. After injection of the mixed solvent charge 551 and solute 563 through hollow injection needle 523 into target tissue, the direction of force on piston shaft head 549 is reversed, thus causing the withdrawal of the cartridge 531 and injection needle 523 to reside completely within cartridge housing 501.

FIG. 6 shows an embodiment of the present invention differing from the other described embodiments in that the separation barrier and the separation barrier attachment groove is recessed past the line of descent of the piston to allow passage thereof through the breached separation barrier and wherein the barrier breaching device is activated by an electromagnet or electronically actuated pin embedded in the wall of the substantially circular cartridge housing.

With reference to FIG. 6 two-component cartridge syringe comprises a double ended substantially cylindrical cartridge housing 601 having a conically tapered injection end constructed of a rigid material suitable for injection molding such as linear polypropylene or polystyrene. A housing is provided with cartridge residence chamber 615 and a cavity 613 for an electromagnet 623. The lower end of cartridge housing 601, tip 616, is significantly thinned and made of easily puncturable material in order to allow a needle 618 to puncture a tip 616 when a cartridge 631 descends. Cartridge housing 601 is provided with a puncturable end cap 603 that also functions as a shock absorber when the cartridge 631 bottoms out.

Cylindrical cartridge 631, of rigid material such as Boron glass, is slidably positioned within cartridge housing 601 and is provided with a two-portion chamber in which is provided a solvent charge 651 and a solute charge 663. Solvent charge 651 is stored in a first portion 633 of cartridge 631, while solute charge 663 is stored in a second portion 635. A rectangular glass wall protrusion 634 is provided in cartridge 631 to allow a membrane seat 671 to be recessed out of the line of descent of a piston 645. First portion 633 is separated from second portion 635 by membrane seat 671, a resilient circular U channel cast from silicone rubber which is rigidly attached to attachment on groove 632 of glass wall protrusion 634, either by pressure generated by oversizing the diameter of the membrane seat wall 636 adjacent to the attachment groove 632 or an industrial adhesive known in the art into which is fitted a puncturable membrane 673 such as a hydrophobic coated polystyrene film of 0.005" which film has the property of being shattered when pricked. The film is locked in by an O-ring (not shown). A permanent magnet N 637 is held in place on the glass wall of cartridge 631 by silicone grease and which has the property, in a thin layer, 0.005–1.000" of acting as temporary adhesive. Rigidly attached to permanent magnet N 637 is a pin 638. A permeable tray 640 holds solute charge 663. N and S as used in magnets are conventions for opposite magnetic charges.

The above described embodiment of the mixing syringe operates as described herein below.

Cartridge 631 is propelled toward sealing end cap 603 by the application of force to plunger shaft head 649 in the direction of end cap 603 which force is communicated through the plunger shaft to piston 645 thus applying hydraulic pressure through solvent charge 651 and membrane seat 671 forcing cartridge 631 and permanently attached needle assembly 693 toward end cap 603 causing cartridge 631 to slide down cartridge housing 601. As cartridge 631 moves toward end cap 603, glass wall protrusion 634 trips contact switch 655 which closes the circuit (not shown) of battery 642 causing current to flow through magnetic windings 643 causing electromagnet 623 to be magnetic charged N and holding firmly in place relative to cartridge housing 601 permanent magnet S 637 and attached pin 638. As cartridge 631 continues in motion toward end cap 603 as seen in FIG. 6(b), pin 638 causes burstable membrane 673 to burst allowing solute charge 651 to enter into second portion 635 of cartridge 631. Piston 645 continues to propel cartridge 631 towards sealable end cap 603 propelling needle 618 into target tissue. When cartridge 631 is seated onto end cap 603 the force toward end cap 603 on piston 645 will cause the piston to move toward end cap 603 as shown in FIG. 6(c) forcing permanent magnet S to be move down the inner glass wall of cartridge 631.

The silicone grease that held permanent magnet S 637 onto the glass walls of cartridge 631 acts as a lubricant for piston 645 and also as an adhesive for magnet with a force of about 3 oz. Piston 645 can pass the recessed membrane seat 671 and expel the solvated solute charge through hollow needle 618 into target tissue. The embodiment of the invention shown in FIG. 7 illustrates a variation of that shown in FIG. 1 but having a modified injection needle which also functions as a pushrod to burst a burstable barrier separating the two cartridge portions.

Figure 7:
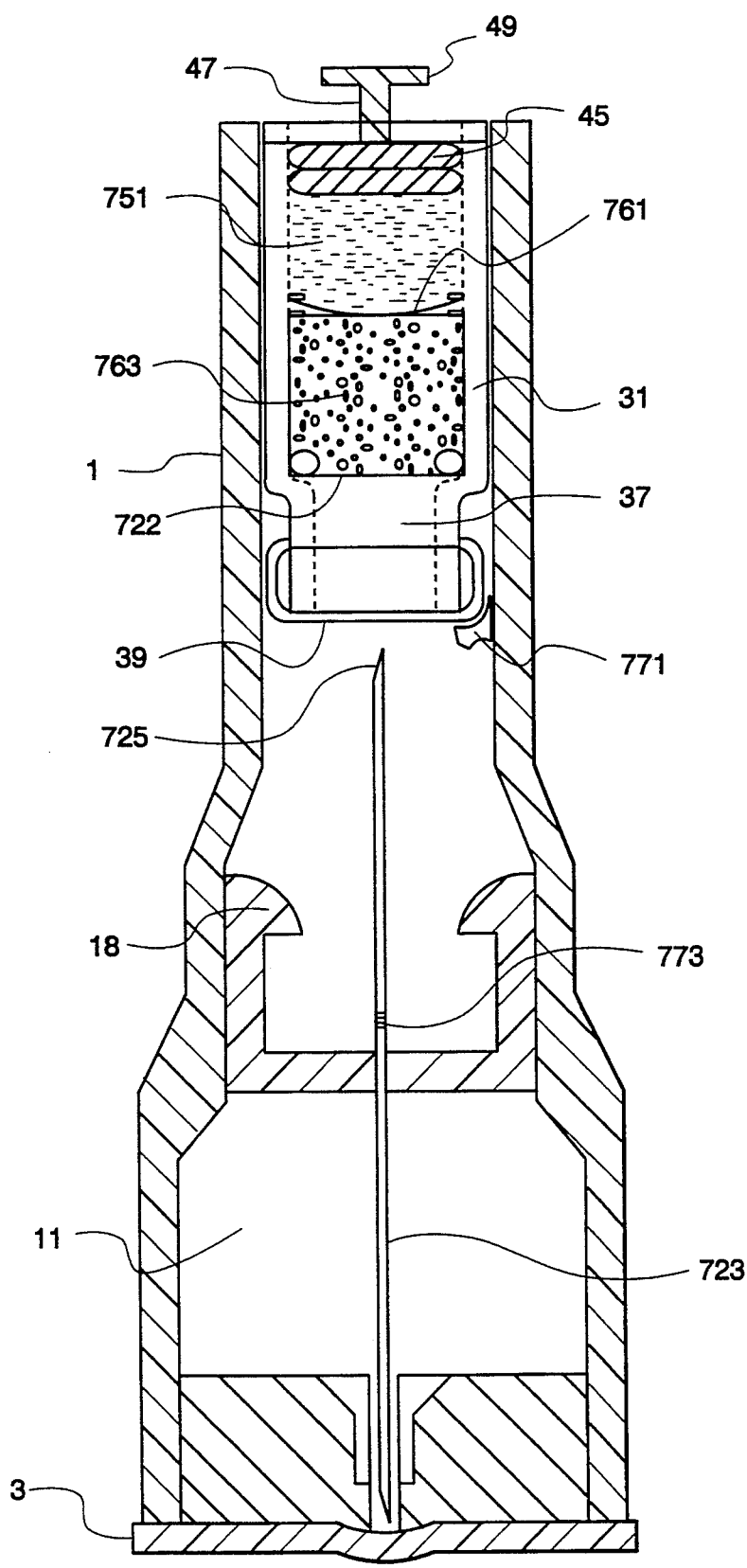
FIG. 7 is a sectional elevation view of a cartridge syringe constructed in accordance with another embodiment of the invention similar to that shown in FIG. 1 but wherein the extended injection needle also performs the barrier breaching function of a pushrod.

With reference to FIG. 7 cylindrical cartridge 31 of rigid material such as water glass is slidably positioned within cartridge housing 1 and is provided with a three-portion chamber in which is stored a solvent charge 751 and a solute charge 763. A cartridge solvent portion having solvent 751 therein is separated from the cartridge portion having solute 763 therein by a burstable membrane 761 as in the embodiment shown in FIG. 2, burstable membrane 761 is seated in cartridge 31 by a membrane seat made from vulcanized rubber which is rigidly attached and sealed to the internal walls of cartridge 31 either by pressure generated by oversizing the diameter of the wall adjacent to the cartridge wall or an industrial adhesive known to the art.

The solute storage portion of cartridge 31 is provided with a bead column of ion exchange resins similar to that shown in FIG. 2 which are saturated with the appropriate solute charge to be eluted by solvent charge 751.

Needle assembly housing 18 is provided with a hollow pushrod/injection needle 723 rigidly attached therethrough. Hollow pushrod injection needle 723 is provided with a sharpened pushrod injection needle internal end 725 having no aperture. Hollow pushrod injection needle 723 is also provided with a pushrod injection needle aperture 773 positioned in relation to needle assembly housing 18 such that pushrod injection needle aperture 773 is not exposed to the mixed solvent 751/solute 763 mixture until puncturable cartridge end stopper 39 is seated against the bottom of needle assembly housing 18 during the injection stroke of the device.

The operation of the device shown in FIG. 7 is similar to that shown in the other embodiments, cartridge 31 being impelled by pressure provided through piston shaft head 49 forcing cartridge 31 toward puncturable cartridge housing sealing end cap 3. Such pressure is sufficient to break breakable cartridge positioning tab 771 allowing cartridge 31 to proceed toward puncturable cartridge housing sealing end cap 3. Continued downward pressure on piston head shaft 49 causes pushrod injection needle internal end which has no aperture to puncture puncturable cartridge end stopper 39 bead column 772 and burstable membrane 761. As in the other embodiments disclosed, the breaching of the barrier between the solvent and solute of cartridge 31 permits the joining those two chambers and the mixing of the solute and solvent. The position of pushrod injection needle aperture 773 permits access of the mixed medicament only after third cartridge portion 37 is completely captured and needle assembly housing 18 with third cartridge portion 37 is fully within needle assembly receiving chamber 11.

With reference to FIG. 8, various views of the needle housing of the present invention are shown. FIG. 8(a) shows a perspective view of the needle assembly housing showing needle assembly housing bottom 18 needle assembly housing flanges 19 and needle assembly housing flange lips 21. Injection needle aperture 822 which is configured for the rigid attachment therethrough of an injection needle is also shown.

Figure 8C:
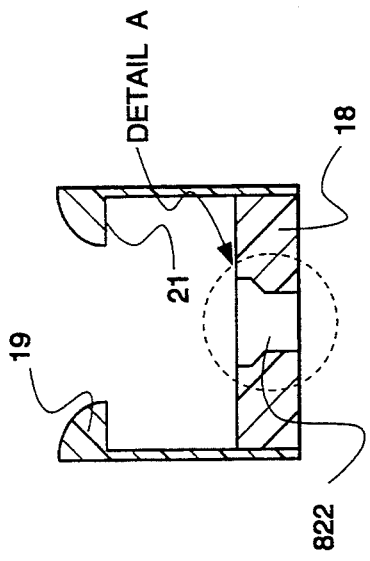
FIG. 8(c) is a sectional view taken along the lines A—A in FIG. 8(c).
Figure 8D:
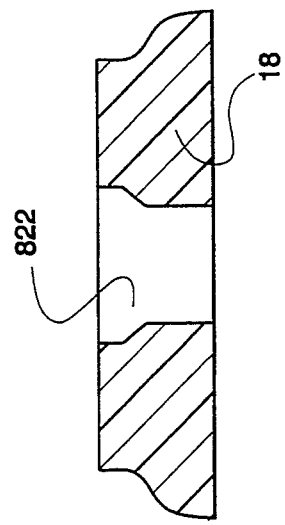
FIG. 8(d) is an enlarged view of Detail A of FIG. 8(c).
Figure 8B:
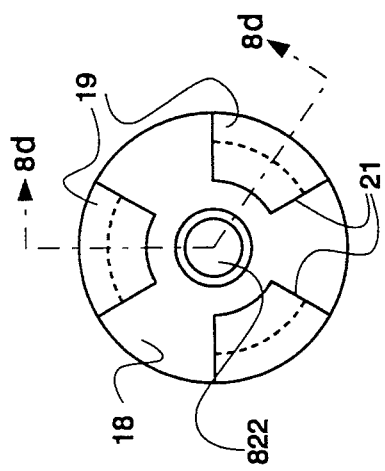
FIG. 8(b) is a plan view of the needle housing assembly of FIG. 8(a).

FIG. 8(b) is a plan view of the housing of the present invention showing housing bottom 18 housing flanges 19 and housing flange lips 21 as well as injection needle aperture 822.

FIG. 8(c) shows a sectional view through section A—A of FIG. 8(b) showing housing bottom 18 housing flanges 19 and housing flange lips 21. In addition, an injection needle aperture 822 is shown disposed through housing bottom 18.

FIG. 8(d) is a detailed cross-sectional view of a portion of FIG. 8(c) showing injection needle aperture 822 in needle assembly housing bottom 18.

Figure 8A:
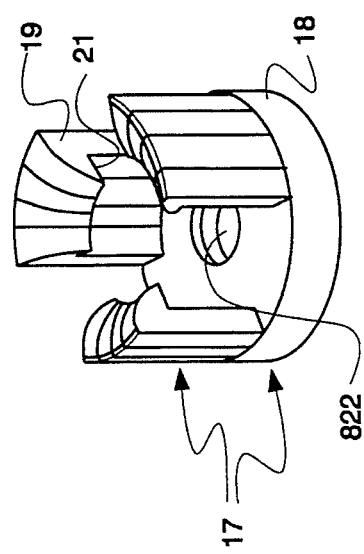
FIG. 8(a) is a perspective view of an embodiment of the needle housing assembly constructed in accordance with the invention which can be used with various necked containers known in the art as well as with various embodiments of the cartridge syringe of the present invention.

As can be seen with reference to FIGS. 8(a), (b), (c), and (d), and with reference to FIGS. 2, 3, 4, and 7, needle assembly housing 17 having an injection needle rigidly affixed therethrough operates in relation to a necked medicament container. More specifically, when the necked end of a medicament container is pressed into contact with the curved abutments of flanges 19 of needle assembly housing 17, the flanges 19 expand to receive the end of the necked medicament container and contract to securely capture the container when flange lips 21 are exposed to the narrowing recess forming the neck of the necked medicament container.

As shown in FIG. 8(a), needle assembly housing bottom 18 has injection needle aperture 822 therethrough for receipt of an injection needle. Such a needle can be molded therein, threaded therethrough, or snap fit therethrough or affixed in any other manner known in the art.

Although a pass-through valve having a barrel-shaped rotor may be adaptable for certain uses, a ball valve having a substantially spherical rotor and seat therefor is another preferred embodiment of the temporary breachable barrier of the invention. The ball valve rotor is provided with a cylindrical aperture therethrough of appropriate dimension so that, when the valve rotor is rotated to align the rotor aperture with the bore of the cartridge cylinder, the cartridge piston can pass sealably therethrough. This can be accomplished by providing the valve rotor with a cylindrical bore substantially identical to the cartridge bore through which the piston moves. Alternatively, by providing a cartridge piston of elastically deformable material such as silicone plastic or rubber which can compress or expand to pass sealably through the valve rotor, the contents of the cartridge can be more completely expelled. The ball valve seat is preferably integral to the cartridge walls and recessed sealably therein sufficiently far to permit the cartridge piston to pass sealably therethrough.

Figure 9C:
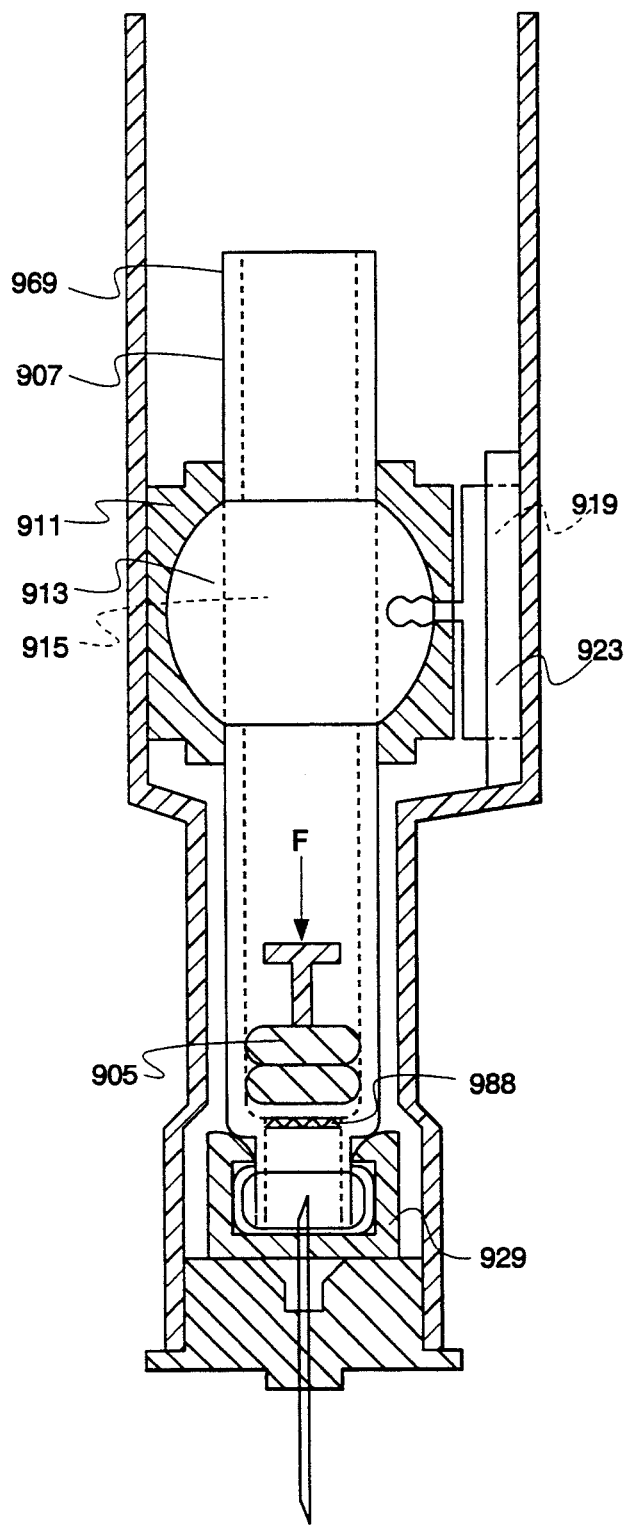
FIG. 9(c) is a sectional elevation view of the cartridge of FIG. 9(a) wherein the ball valve has been opened and the piston has passed sealably therethrough to evacuate the solvent/solute mixture and to become seated at the curved abutments forming the necked portion of the cartridge.
Figure 9D:
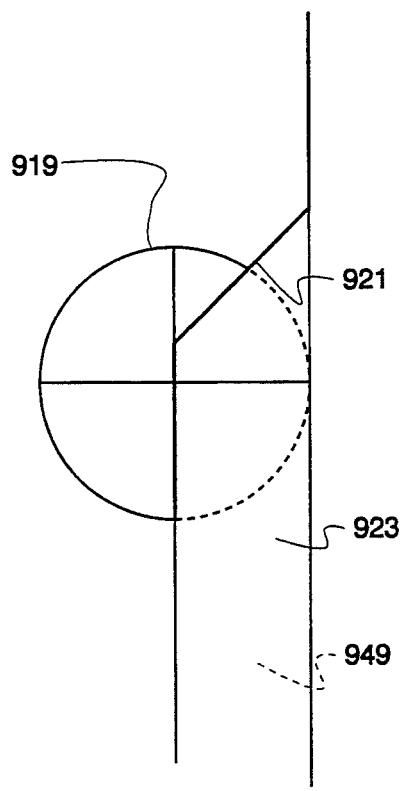
FIG. 9(d) is a detail view of the ball valve operating cam in the open position of FIG. 9(c).

FIGS. 9(a), (b), (c), and (d) illustrate an additional embodiment of the invention wherein the means for separating the two chambers of the cartridge is a ball valve operated in much the same manner as the stopcock shown in FIG. 5. A key aspect of this embodiment of the invention is the passthrough feature of the valve which permits the cartridge piston to pass sealably therethrough, thus evacuating the cartridge more completely.

With references to FIGS. 9(a), (b), (c) and (d), a cartridge housing 909 has a cartridge 981 slidably disposed therein. A cartridge housing 909 also has a needle assembly housing 929 slidably disposed therein between a cartridge 981 and a puncturable cartridge housing sealing end cap 937. A cartridge 981 comprises a glass cylindrical top element 969 having a first cartridge solvent reservoir portion 907 therein and also having a piston 905 slidably seated therein. A cartridge 981 is further provided with a ball valve cast housing 911 having a substantially spherical ball valve 913 seated therein. A ball valve 913 also has a cylindrical channel 915 of a diameter greater than the bore of a cartridge 981.

A cartridge 981 is further provided with a glass element 925 which is attached to the injection end of a ball valve cast housing. A glass element 925 comprises a cartridge neck 927 and a puncturable cartridge end stopper 928. A ball valve 913 is further provided with an operating cam 919 disposed to rotatably engage a guide ridge 923 having an inclined plane 921 and a guide channel 949 disposed therein for guiding and operating a cartridge 981 and a ball valve 913, respectively.

The operation of the embodiment of the present invention shown in FIGS. 9(a), (b), (c) and (d) is very similar to the operation of the embodiment of the invention shown in FIGS. 5(a), (b), (c), (d) and (e). More specifically, force transmitted through a piston shaft head 901, a piston shaft 903, a rubber piston 905 and a solvent charge 906 forces a cartridge 981 toward a puncturable cartridge housing sealing end cap 937. The movement of a cartridge 981 causes a rotatable cam element 943 to engage an inclined plane 921 of a guide ridge 923, thus causing a 90 degree rotation of a rotatable cam element 943 and of a ball valve 913 which is fixedly attached thereto, and causing the alignment of cylindrical aperture 915 with the bore of a first cartridge solvent reservoir portion 907 and with a bore of second cartridge solute portion 979 to such an extent that a rubber piston 905 can pass sealably through a ball valve 913 forcing a solvent charge 906 into a second cartridge solute portion 979 and through a solute grid 988 having a medically active substance disposed therein. The medically active substance is eluted by solvent charge 906 as it passes through a solute grid 988 recessed into the neck portion of a cartridge 981 to permit a piston 905 to almost completely evacuate cartridge 981. Simultaneously with the downward movement of a cartridge 981 is the movement of a needle assembly housing 929 into a needle assembly housing expansion chamber 933 allowing the expansion of the needle assembly housing flanges 926 and the capture of a cartridge neck 927 by a needle assembly housing 929 and the puncturing of puncturable cartridge end stopper 928 by an injection needle internal end 931. Continued pressure on a rubber piston 905 causes the complete expulsion of a solvent charge 906 and the eluted solute contained therein.

Reversing the direction of force placed on a rubber piston 905 causes retraction of a cartridge 981 and an irreversibly captured needle housing assembly 929 so that a cartridge 981, a needle housing assembly 929, and an injection needle 985 reside wholly within a cartridge 981.

TABLE 1

| EMBODIMENT NO. | TYPE OF BARRIER | BREACHING TRIGGER | SOLUTE VEHICLE | MIXING MECHANISM |
|---|---|---|---|---|
| 1 | Wedge plug | Pushrod | Tray | None |
| 2 | Burstable membrane | Pushrod (PIN) | Column of beads | Backpressure of column |
| 3 | Disk valve | 90 degree spiral rod | Packing | Backpressure of packing |
| 4 | Stopcock | External Pushrod | Doughnut prepack | Rotating Paddles |
| 5 | Stopcock | Integral pushrod/cam | Elution Maze | Backpressure of Maze |
| 6 | Pass-through membrane | Electromagnetic pin | Tray column | Backpressure of column |
| 7 | Burstable membrane | Pushrod/ Injection needle | Bead column | Backpressure of column |
| 9 | Pass-through stopcock | Integral pushrod/cam | Grid in Cartridge Neck | Backpressure of prepack |

Table 1 lists some major characteristics of the eight embodiments of the cartridge shown in FIGS. 1–7 and 9. The listed combinations of elements are illustrative only and are intended to demonstrate some of the permutations of the invention. For example, although not shown in the drawings or table, it is obvious from the description herein that a passthrough stopcock can be substituted for the stopcock in Embodiment No. 5. Similarly, an elution maze can be substituted for the bead columns of Embodiment Nos. 7 or 2.

Thus, with reference to FIGS. 1–9, it can be clearly seen that by performing only the simple operation of applying downward pressure on the operating piston of any of the various embodiments of the present invention, that joining of the solvent and solute chambers, mixing of the two medicament components, and the injection of the medically active substance is achieved. It can also be clearly seen that the simple operation of reversing the direction of force on the operating piston, that the injection needle is both withdrawn from the injection site and withdrawn to reside wholly within the cartridge housing of the invention.

Thus the present invention provides a series of embodiments wherein the relative motion of a prepackaged cartridge containing at least one medically active substance and a housing for the cartridge triggers the breaching of a barrier between a cartridge chamber having the medically active substance therein and another cartridge chamber containing a physiologically acceptable solvent or diluent.

Preferred methods of using the two-component syringes of the types described above are both with an adaptor for manual use and with an automatic injection/aspiration device of the type described in parent application Ser. No. 641,752, pending, of which the instant application is a continuation-in-part.

With reference to the resilient materials disclosed herein, such materials are those standard in the medical and dental packaging and hypodermic syringe art such as rubber, plastics, and other synthetic and non-synthetic materials known in the art for use in fulfilling similar and related objectives. It is also clear that all of the embodiments of the invention disclosed herein are adapted to be manufactured by standard medical and dental container and device manufacturing equipment.

Also, the cartridges of the present invention are adapted to contain standard amounts of solvent and appropriate amounts of solute for standard dosages of the particular medically active substance to be administered.

"Cylindrical" means having a shape or cavity described by a line which always has a point in common with a given closed curve, and which line moves so that it is always parallel with a given line not in the plane of the closed curve. Thus, a right circular cylinder is one having two equal parallel circular bases and a perpendicular axis, and a right elliptical cylinder is one having two equal parallel elliptical bases and a perpendicular axis. In the context of the invention, it can be seen that the relationship between the various cartridge embodiments and their corresponding cartridge housings is that of a piston fitted to a cylinder. That is, the cartridge housing bore (cylinder) acts as both container and guide for the cartridge (piston) as the device operates. With respect to the various pistons of the cartridges, each operates much the same as a standard syringe plunger known in the art.

By "substantially cylindrical" it is meant that the housing and corresponding cartridge and needle housing assembly of a particular embodiment of the invention are of appropriate relative configuration, though not precisely cylinders, that the relative movement of the various components approximates the action of a piston or pistons within a cylinder.

By "sealably" with regard to piston movement through a breachable temporary barrier means is meant sealed sufficiently while moving through the breachable barrier that fluid is driven therethrough by the piston.

What is claimed is:

1. A mixing syringe for two-component medicaments comprising:
(A) a cartridge housing having a first end and a second end, said cartridge housing having a substantially cylindrical cartridge housing bore;

(B) a slidable cartridge disposed in said cartridge housing bore and having a first end, a second end, and a temporary sealing barrier disposed between said first and second ends and separating a cartridge bore of said cartridge into a cylindrical medicament solvent charge chamber and a cylindrical medicament charge chamber, said cartridge housing having means connected thereto, for breaching said temporary sealing barrier, said cartridge being suitable for separately storing a medicament solvent charge and a medicament charge in said medicament solvent charge chamber and said medicament charge chamber, respectively, said charges to be mixed to form a medicament to be expelled from said cartridge;

(C) a piston disposed within said first end of said cartridge and being slidably seated in said cartridge bore;

(D) a retractable needle housing assembly slidable in said cartridge housing;

(E) a retractable injection needle fixedly attached to said needle housing assembly and extending therethrough for injecting mixed medicament; and (F) a puncturable cartridge end stopper rigidly attached to and sealing said second end of said cartridge;

said means for breaching the temporary sealing barrier between chambers of said slidable cartridge comprising a pushrod having an anchoring end and a puncturing end wherein said anchoring end is connected to said cartridge housing, said pushrod extending from said cartridge housing toward said cartridge puncturable end stopper;

said needle assembly housing having a pushrod aperture for freely guiding said pushrod therethrough so that said puncturing end of said pushrod resides in close proximity to and in alignment with said puncturable cartridge end stopper.

2. The device of claim 1 wherein said breachable temporary sealing barrier comprises a membrane.

3. The device of claim 2 wherein said membrane comprises a synthetic polymer.

4. The device of claim 3 wherein said polymer is polystyrene.

5. The device of claim 2 wherein said membrane comprises rubber.

6. The device of claim 3 wherein said polymer is polyethylene.

7. The device of claim 1 wherein said needle housing assembly is slidably disposed in said cylindrical bore of said cartridge housing and wherein said injection needle comprises a hollow shaft, an internal end, an internal shaft portion, an external end, an external shaft portion, first and second apertures, and a passageway extending through said hollow shaft and connecting said first and second apertures, said needle being rigidly attached to and extending through said needle housing, said internal end of said needle extending through said needle assembly housing toward said puncturable cartridge end stopper, said external end of said needle extending toward said puncturable end cap of said cartridge housing without protruding therefrom, said needle being adapted to expel a medicament from said cartridge, said housing having locking means for irreversibly locking said needle assembly housing to said cartridge when said needle cap assembly and said cartridge are a predetermined distance apart.

8. The device of claim 7 wherein said first injection needle aperture is disposed in said internal needle shaft portion an appropriate distance from said housing to receive fluid from a punctured medicament cartridge, and said second injection needle aperture is disposed in said external needle end.

9. The device of claim 7 wherein said first injection needle aperture is disposed in said internal needle shaft end, and said second injection needle aperture is disposed in said external needle end.

10. The device of claim 1 wherein said cartridge housing further comprises (G) a puncturable end cap, said end cap sealing said second end of said cartridge housing and having a needle guide disposed therein.

11. The device of claim 1 wherein said piston further comprises (H) an operating shaft for operating said piston and said cartridge and for adapting said cartridge to other devices.

12. The device of claim 1 wherein said means fixedly attached to said cartridge housing for breaching a temporary sealing barrier between chambers of said slidable cartridge comprises a pushrod.

13. A mixing syringe for two-component medicaments comprising:

(A) a cartridge housing having a first end and a second end, said cartridge housing having a substantially cylindrical cartridge housing bore;

(B) a slidable cartridge disposed in said cartridge housing bore and having a first end, a second end, and a temporary sealing barrier disposed between said first and second ends and separating a cartridge bore of said cartridge into a cylindrical medicament solvent charge chamber and a cylindrical medicament charge chamber, said cartridge housing having means connected thereto, for breaching said temporary sealing barrier, said cartridge being suitable for separately storing a medicament solvent charge and a medicament charge in said medicament solvent charge chamber and said medicament charge chamber, respectively, said charges to be mixed to form a medicament to be expelled from said cartridge;

(C) a piston disposed within said first end of said cartridge and being slidably seated in said cartridge bore;

(D) a needle housing assembly rigidly attached to said cartridge and contained wholly within said cartridge housing;

(E) an injection needle which is containable wholly within said cartridge housing, which can be extended to a position in which at least a portion of said needle extends outside of said cartridge housing, said needle being fixedly attached to said needle housing assembly and extending therethrough for injecting mixed medicament;

(F) a puncturable end cap, said end cap sealing said second end of said cartridge housing; and (G) means for retracting said needle to reside completely within said cartridge housing after the expulsion of said medicament from said syringe;

said means for breaching the temporary sealing barrier between chambers of said slidable cartridge comprising a pushrod having an anchoring end and a puncturing end wherein said anchoring end is connected to said cartridge housing, said pushrod extending from said cartridge housing toward said cartridge puncturable end stopper;

said needle assembly housing having a pushrod aperture for freely guiding said pushrod therethrough so that said puncturing end of said pushrod resides in close proximity to and in alignment with said puncturable cartridge end stopper.

* * * * *